United States Patent
Pacetti et al.

(10) Patent No.: US 9,999,527 B2
(45) Date of Patent: Jun. 19, 2018

(54) SCAFFOLDS HAVING RADIOPAQUE MARKERS

(71) Applicant: Abbott Cardiovascular Systems Inc., Santa Clara, CA (US)

(72) Inventors: Stephen Pacetti, San Jose, CA (US); Joan Bei, Palo Alto, CA (US); Karen Wang, Cupertino, CA (US); Annie Liu, Cupertino, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 255 days.

(21) Appl. No.: 14/620,096

(22) Filed: Feb. 11, 2015

(65) Prior Publication Data
US 2016/0228267 A1   Aug. 11, 2016

(51) Int. Cl.
*A61F 2/82* (2013.01)
*A61L 31/04* (2006.01)
(Continued)

(52) U.S. Cl.
CPC .............. *A61F 2/82* (2013.01); *A61F 2/915* (2013.01); *A61L 31/04* (2013.01); *A61L 31/18* (2013.01); *A61F 2002/91533* (2013.01); *A61F 2002/91575* (2013.01); *A61F 2210/0004* (2013.01); *A61F 2210/0071* (2013.01); *A61F 2240/001* (2013.01); *A61F 2250/0098* (2013.01)

(58) Field of Classification Search
CPC ......... Y10T 29/49826; Y10T 29/49865; Y10T 29/49876; Y10T 29/49908; Y10T 29/4992; Y10T 29/53952; Y10T 29/53987; Y10T 29/53996; B21J 15/02; A61F 2/82; A61F 2/915; A61F 2210/0004; A61F 2002/91533; A61F 2002/91575; A61F 2210/0071; A61F 2240/001; A61F 2250/0098; A61L 31/18; A61L 31/04
USPC ................. 29/428, 525.06; 264/263, 279
See application file for complete search history.

(56) References Cited

U.S. PATENT DOCUMENTS

| 2,697,863 A | 12/1954 | Moser |
| 3,476,463 A | 11/1969 | Kreuzer |

(Continued)

FOREIGN PATENT DOCUMENTS

| CN | 1241442 | 1/2000 |
| DE | 44 07 079 | 9/1994 |

(Continued)

OTHER PUBLICATIONS

International Search Report and Written Opinion dated Jun. 29, 2016 in International Patent Application No. PCT/US2016/017333, 13 pages.

(Continued)

*Primary Examiner* — Sarang Afzali
*Assistant Examiner* — Darrell C Ford
(74) *Attorney, Agent, or Firm* — Squire Patton Boggs (US) LLP

(57) ABSTRACT

A scaffold includes a radiopaque marker connected to a strut. The marker is retained within the strut by one or more of a mechanical interference fit, a polymer coating or melt, and/or by friction. The marker can take the form of a bead, rivet or snap-in marker, or a tube deformed when attached to the strut. The strut is made from a tube. The strut has a thickness of about 100 microns.

13 Claims, 10 Drawing Sheets

(51) Int. Cl.
*A61F 2/915* (2013.01)
*A61L 31/18* (2006.01)
*B23P 17/00* (2006.01)
*B29C 45/14* (2006.01)

(56) References Cited

U.S. PATENT DOCUMENTS

| | | | |
|---|---|---|---|
| 3,687,435 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,800,882 A | 1/1989 | Gianturco | |
| 4,816,339 A | 3/1989 | Tu et al. | |
| 4,818,559 A | 4/1989 | Hama et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,886,870 A | 12/1989 | D'Amore et al. | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,061,281 A | 10/1991 | Mares et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury | |
| 5,356,433 A | 10/1994 | Rowland et al. | |
| 5,380,976 A | 1/1995 | Couch | |
| 5,383,925 A | 1/1995 | Schmitt | |
| 5,385,580 A | 1/1995 | Schmitt | |
| 5,389,106 A | 2/1995 | Tower | |
| 5,399,666 A | 3/1995 | Ford | |
| 5,423,885 A | 6/1995 | Williams | |
| 5,441,515 A | 8/1995 | Khosravi et al. | |
| 5,443,458 A | 8/1995 | Eury et al. | |
| 5,443,500 A | 8/1995 | Sigwart | |
| 5,455,040 A | 10/1995 | Marchant | |
| 5,464,650 A | 11/1995 | Berg et al. | |
| 5,486,546 A | 1/1996 | Mathiesen et al. | |
| 5,500,013 A | 3/1996 | Buscemi et al. | |
| 5,502,158 A | 3/1996 | Sinclair et al. | |
| 5,507,799 A | 4/1996 | Sumiya | |
| 5,514,379 A | 5/1996 | Weissleder et al. | |
| 5,525,646 A | 6/1996 | Lundgren et al. | |
| 5,527,337 A | 6/1996 | Stack et al. | |
| 5,545,408 A | 8/1996 | Trigg et al. | |
| 5,554,120 A | 9/1996 | Chen et al. | |
| 5,556,413 A | 9/1996 | Lam | |
| 5,565,215 A | 10/1996 | Gref et al. | |
| 5,578,046 A | 11/1996 | Liu et al. | |
| 5,578,073 A | 11/1996 | Haimovich et al. | |
| 5,591,199 A | 1/1997 | Porter et al. | |
| 5,591,607 A | 1/1997 | Gryaznov | |
| 5,593,403 A | 1/1997 | Buscemi | |
| 5,593,434 A | 1/1997 | Williams | |
| 5,599,301 A | 2/1997 | Jacobs et al. | |
| 5,599,922 A | 2/1997 | Gryaznov et al. | |
| 5,603,722 A | 2/1997 | Phan et al. | |
| 5,605,696 A | 2/1997 | Eury et al. | |
| 5,607,442 A | 3/1997 | Fischell et al. | |
| 5,607,467 A | 3/1997 | Froix | |
| 5,618,299 A | 4/1997 | Khosravi et al. | |
| 5,629,077 A | 5/1997 | Turnlund et al. | |
| 5,631,135 A | 5/1997 | Gryaznov et al. | |
| 5,632,771 A | 5/1997 | Boatman et al. | |
| 5,632,840 A | 5/1997 | Campbell | |
| 5,637,113 A | 6/1997 | Tartaglia et al. | |
| 5,649,977 A | 7/1997 | Campbell | |
| 5,656,186 A | 8/1997 | Mourou et al. | |
| 5,667,767 A | 9/1997 | Greff et al. | |
| 5,667,796 A | 9/1997 | Otten | |
| 5,670,161 A | 9/1997 | Healy et al. | |
| 5,670,558 A | 9/1997 | Onishi et al. | |
| 5,686,540 A | 11/1997 | Kakizawa | |
| 5,693,085 A | 12/1997 | Buirge et al. | |
| 5,700,286 A | 12/1997 | Tartaglia et al. | |
| 5,700,901 A | 12/1997 | Hurst et al. | |
| 5,704,082 A | 1/1998 | Smith | |
| 5,707,385 A | 1/1998 | Williams | |
| 5,711,763 A | 1/1998 | Nonami et al. | |
| 5,716,981 A | 2/1998 | Hunter et al. | |
| 5,725,549 A | 3/1998 | Lam | |
| 5,725,572 A | 3/1998 | Lam et al. | |
| 5,726,297 A | 3/1998 | Gryaznov et al. | |
| 5,728,751 A | 3/1998 | Patnaik | |
| 5,733,326 A | 3/1998 | Tomonto et al. | |
| 5,733,330 A | 3/1998 | Cox | |
| 5,733,564 A | 3/1998 | Lehtinen | |
| 5,733,925 A | 3/1998 | Kunz et al. | |
| 5,741,327 A * | 4/1998 | Frantzen | A61F 2/91 606/153 |
| 5,741,881 A | 4/1998 | Patnaik | |
| 5,756,457 A | 5/1998 | Wang et al. | |
| 5,756,476 A | 5/1998 | Epstein et al. | |
| 5,765,682 A | 6/1998 | Bley et al. | |
| 5,766,204 A | 6/1998 | Porter et al. | |
| 5,766,239 A | 6/1998 | Cox | |
| 5,766,710 A | 6/1998 | Turnlund et al. | |
| 5,769,883 A | 6/1998 | Buscemi et al. | |
| 5,770,609 A | 6/1998 | Grainger et al. | |
| 5,780,807 A | 7/1998 | Saunders | |
| 5,800,516 A | 9/1998 | Fine et al. | |
| 5,811,447 A | 9/1998 | Kunz et al. | |
| 5,824,042 A | 10/1998 | Lombardi et al. | |
| 5,824,049 A | 10/1998 | Ragheb et al. | |

(56) References Cited

U.S. PATENT DOCUMENTS

| | | |
|---|---|---|
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,007,845 A | 12/1999 | Domb et al. |
| 6,010,445 A | 1/2000 | Armini et al. |
| 6,015,541 A | 1/2000 | Greff et al. |
| 6,022,374 A * | 2/2000 | Imran ..................... A61F 2/91 623/1.34 |
| 6,042,606 A | 3/2000 | Frantzen |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,095,525 A | 8/2000 | Patnaik |
| 6,096,070 A | 8/2000 | Ragheb et al. |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,110,483 A | 8/2000 | Whitbourne et al. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,131,266 A | 10/2000 | Saunders |
| 6,150,630 A | 11/2000 | Perry et al. |
| 6,153,252 A | 11/2000 | Hossainy et al. |
| 4,776,337 B1 | 12/2000 | Palmaz |
| 6,156,062 A | 12/2000 | McGuinness |
| 6,159,951 A | 12/2000 | Karpeisky et al. |
| 6,160,084 A | 12/2000 | Langer et al. |
| 6,160,240 A | 12/2000 | Momma et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,326 B1 | 1/2001 | Kitaoka et al. |
| 6,174,329 B1 | 1/2001 | Callol et al. |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,206,911 B1 * | 3/2001 | Milo ..................... A61F 2/91 623/1.15 |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,254,632 B1 | 7/2001 | Wu et al. |
| 6,260,976 B1 | 7/2001 | Endou et al. |
| 6,273,913 B1 | 8/2001 | Wright et al. |
| 6,281,262 B1 | 8/2001 | Shikinami |
| 6,283,234 B1 | 9/2001 | Torbet |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,295,168 B1 | 9/2001 | Hofnagle et al. |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,334,871 B1 * | 1/2002 | Dor ..................... A61F 2/91 623/1.34 |
| 6,355,058 B1 | 3/2002 | Pacetti et al. |
| 6,361,557 B1 * | 3/2002 | Gittings ..................... A61F 2/07 606/151 |
| 6,375,826 B1 | 4/2002 | Wang et al. |
| 6,379,381 B1 * | 4/2002 | Hossainy ............. A61L 31/146 623/1.15 |
| 6,387,121 B1 | 5/2002 | Alt |
| 6,388,043 B1 | 5/2002 | Langer et al. |
| 6,395,326 B1 | 5/2002 | Castro et al. |
| 6,402,777 B1 * | 6/2002 | Globerman ............... A61F 2/91 623/1.11 |
| 6,409,752 B1 | 6/2002 | Boatman et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,471,721 B1 | 10/2002 | Dang |
| 6,475,779 B2 | 11/2002 | Mathiowithz et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,506,437 B1 | 1/2003 | Harish et al. |
| 6,511,748 B1 | 1/2003 | Barrows |
| 6,517,888 B1 | 2/2003 | Weber |
| 6,521,865 B1 | 2/2003 | Jones et al. |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |

(56) References Cited

U.S. PATENT DOCUMENTS

| | | | |
|---|---|---|---|
| 6,554,854 B1* | 4/2003 | Flanagan | B23K 26/244 623/1.1 |
| 6,563,080 B2 | 5/2003 | Shapovalov et al. | |
| 6,563,998 B1 | 5/2003 | Farah et al. | |
| 6,565,599 B1 | 5/2003 | Hong et al. | |
| 6,569,191 B1 | 5/2003 | Hogan | |
| 6,569,193 B1 | 5/2003 | Cox et al. | |
| 6,572,672 B2 | 6/2003 | Yadav et al. | |
| 6,574,851 B1 | 6/2003 | Mirizzi | |
| 6,582,472 B2 | 6/2003 | Hart | |
| 6,585,755 B2 | 7/2003 | Jackson et al. | |
| 6,585,765 B1 | 7/2003 | Hossainy et al. | |
| 6,589,227 B2 | 7/2003 | Sonderskov | |
| 6,592,614 B2 | 7/2003 | Lenker et al. | |
| 6,592,617 B2 | 7/2003 | Thompson | |
| 6,613,072 B2 | 9/2003 | Lau et al. | |
| 6,620,194 B2 | 9/2003 | Ding et al. | |
| 6,626,936 B2 | 9/2003 | Stinson | |
| 6,626,939 B1 | 9/2003 | Burnside et al. | |
| 6,635,269 B1 | 10/2003 | Jennissen | |
| 6,641,607 B1 | 11/2003 | Hossainy et al. | |
| 6,645,243 B2 | 11/2003 | Vallana et al. | |
| 6,652,579 B1 | 11/2003 | Cox et al. | |
| 6,656,162 B2 | 12/2003 | Santini, Jr. et al. | |
| 6,664,335 B2 | 12/2003 | Krishnan | |
| 6,666,214 B2 | 12/2003 | Canham | |
| 6,667,049 B2 | 12/2003 | Janas et al. | |
| 6,669,722 B2 | 12/2003 | Chen et al. | |
| 6,669,723 B2 | 12/2003 | Killion et al. | |
| 6,676,697 B1 | 1/2004 | Richter | |
| 6,679,980 B1 | 1/2004 | Andreacchi | |
| 6,689,375 B1 | 2/2004 | Wahlig et al. | |
| 6,695,920 B1 | 2/2004 | Pacetti et al. | |
| 6,696,667 B1 | 2/2004 | Flanagan | |
| 6,699,278 B2 | 3/2004 | Fischell et al. | |
| 6,706,273 B1 | 3/2004 | Roessler | |
| 6,709,379 B1 | 3/2004 | Brandau et al. | |
| 6,719,934 B2 | 4/2004 | Stinson | |
| 6,719,989 B1 | 4/2004 | Matsushima et al. | |
| 6,720,402 B2 | 4/2004 | Langer et al. | |
| 6,746,773 B2 | 6/2004 | Llanos et al. | |
| 6,752,826 B2 | 6/2004 | Holloway et al. | |
| 6,753,007 B2 | 6/2004 | Haggard et al. | |
| 6,764,505 B1 | 7/2004 | Hossainy et al. | |
| 6,780,261 B2 | 8/2004 | Trozera | |
| 6,801,368 B2 | 10/2004 | Coufal et al. | |
| 6,805,898 B1 | 10/2004 | Wu et al. | |
| 6,818,063 B1 | 11/2004 | Kerrigan | |
| 6,822,186 B2 | 11/2004 | Strassl et al. | |
| 6,846,323 B2 | 1/2005 | Yip et al. | |
| 6,852,946 B2 | 2/2005 | Groen et al. | |
| 6,858,680 B2 | 2/2005 | Gunatillake et al. | |
| 6,863,685 B2 | 3/2005 | Davila et al. | |
| 6,867,389 B2 | 3/2005 | Shapovalov et al. | |
| 6,878,758 B2 | 4/2005 | Martin et al. | |
| 6,891,126 B2 | 5/2005 | Matile | |
| 6,899,729 B1 | 5/2005 | Cox et al. | |
| 6,911,041 B1 | 6/2005 | Zscheeg | |
| 6,913,762 B2 | 7/2005 | Caplice et al. | |
| 6,918,928 B2 | 7/2005 | Wolinsky et al. | |
| 6,926,733 B2 | 8/2005 | Stinson | |
| 6,943,964 B1 | 9/2005 | Zhang et al. | |
| 6,981,982 B2 | 1/2006 | Amstrong et al. | |
| 6,981,987 B2 | 1/2006 | Huxel et al. | |
| 7,022,132 B2 | 4/2006 | Kocur | |
| 7,128,737 B1 | 10/2006 | Goder et al. | |
| 7,163,555 B2 | 1/2007 | Dinh | |
| 7,166,099 B2 | 1/2007 | Devens, Jr. | |
| 7,226,475 B2 | 6/2007 | Lenz et al. | |
| 7,243,408 B2 | 7/2007 | Vietmeier | |
| 7,326,245 B2 | 2/2008 | Rosenthal et al. | |
| 7,331,986 B2 | 2/2008 | Brown et al. | |
| 7,500,988 B1 | 3/2009 | Butaric et al. | |
| 7,776,926 B1 | 8/2010 | Hossainy et al. | |
| 8,002,817 B2 | 8/2011 | Limon | |
| 8,303,644 B2 | 11/2012 | Lord et al. | |
| 8,388,673 B2 | 3/2013 | Yang et al. | |
| 8,539,663 B2* | 9/2013 | Wang | A61F 2/95 29/505 |
| 8,752,268 B2 | 6/2014 | Wu | |
| 9,345,597 B2* | 5/2016 | Pacetti | A61F 2/89 |
| 9,532,888 B2 | 1/2017 | Dugan et al. | |
| 2001/0001317 A1 | 5/2001 | Duerig et al. | |
| 2001/0010003 A1* | 7/2001 | Lai | A61F 9/00804 606/107 |
| 2001/0021871 A1 | 9/2001 | Stinson | |
| 2001/0021873 A1 | 9/2001 | Stinson | |
| 2001/0027339 A1 | 10/2001 | Boatman et al. | |
| 2001/0029398 A1 | 10/2001 | Jadhav | |
| 2001/0044652 A1 | 11/2001 | Moore | |
| 2002/0002399 A1 | 1/2002 | Huxel et al. | |
| 2002/0004060 A1 | 1/2002 | Heublein et al. | |
| 2002/0004101 A1 | 1/2002 | Ding et al. | |
| 2002/0032486 A1 | 3/2002 | Lazarovitz et al. | |
| 2002/0062148 A1 | 5/2002 | Hart | |
| 2002/0065553 A1 | 5/2002 | Weber | |
| 2002/0111590 A1* | 8/2002 | Davila | A61B 17/0644 604/265 |
| 2002/0116050 A1 | 8/2002 | Kocur | |
| 2002/0138133 A1 | 9/2002 | Lenz et al. | |
| 2002/0143386 A1 | 10/2002 | Davila et al. | |
| 2002/0161114 A1 | 10/2002 | Gunatillake et al. | |
| 2002/0190038 A1 | 12/2002 | Lawson | |
| 2002/0193862 A1 | 12/2002 | Mitelberg et al. | |
| 2003/0004563 A1 | 1/2003 | Jackson et al. | |
| 2003/0009235 A1* | 1/2003 | Manrique | A61B 17/866 623/23.63 |
| 2003/0028241 A1 | 2/2003 | Stinson | |
| 2003/0028245 A1 | 2/2003 | Barclay et al. | |
| 2003/0033001 A1 | 2/2003 | Igaki | |
| 2003/0039689 A1 | 2/2003 | Chen et al. | |
| 2003/0050688 A1 | 3/2003 | Fischell et al. | |
| 2003/0060872 A1* | 3/2003 | Gomringer | A61F 2/91 623/1.15 |
| 2003/0065355 A1 | 4/2003 | Weber | |
| 2003/0069630 A1 | 4/2003 | Burgermeister et al. | |
| 2003/0093107 A1 | 5/2003 | Parsonage et al. | |
| 2003/0100865 A1 | 5/2003 | Santini, Jr. et al. | |
| 2003/0105518 A1 | 6/2003 | Dutta | |
| 2003/0105530 A1 | 6/2003 | Pirhonen | |
| 2003/0108588 A1 | 6/2003 | Chen | |
| 2003/0121148 A1 | 7/2003 | DiCaprio | |
| 2003/0153971 A1 | 8/2003 | Chandrasekaran | |
| 2003/0155328 A1 | 8/2003 | Huth et al. | |
| 2003/0171053 A1 | 9/2003 | Sanders | |
| 2003/0187495 A1 | 10/2003 | Cully et al. | |
| 2003/0204245 A1 | 10/2003 | Brightbill | |
| 2003/0208259 A1 | 11/2003 | Penhasi | |
| 2003/0209835 A1 | 11/2003 | Chun et al. | |
| 2003/0226833 A1 | 12/2003 | Shapovalov et al. | |
| 2003/0236563 A1 | 12/2003 | Fifer | |
| 2004/0015228 A1 | 1/2004 | Lombardi et al. | |
| 2004/0024449 A1 | 2/2004 | Boyle | |
| 2004/0027339 A1 | 2/2004 | Schulz | |
| 2004/0044399 A1 | 3/2004 | Ventura | |
| 2004/0073291 A1 | 4/2004 | Brown et al. | |
| 2004/0078071 A1* | 4/2004 | Escamilla | A61B 17/12022 623/1.11 |
| 2004/0088039 A1* | 5/2004 | Lee | A61F 2/91 623/1.15 |
| 2004/0093077 A1 | 5/2004 | White et al. | |
| 2004/0098090 A1 | 5/2004 | Williams et al. | |
| 2004/0098095 A1 | 5/2004 | Burnside et al. | |
| 2004/0102758 A1* | 5/2004 | Davila | A61B 17/0644 604/500 |
| 2004/0106987 A1 | 6/2004 | Palasis et al. | |
| 2004/0111149 A1 | 6/2004 | Stinson | |
| 2004/0122509 A1 | 6/2004 | Brodeur | |
| 2004/0125405 A1 | 7/2004 | Sahatjian | |
| 2004/0127970 A1 | 7/2004 | Saunders et al. | |
| 2004/0143180 A1 | 7/2004 | Zhong et al. | |
| 2004/0143317 A1 | 7/2004 | Stinson et al. | |
| 2004/0167610 A1 | 8/2004 | Fleming, III | |

(56) References Cited

U.S. PATENT DOCUMENTS

| | | |
|---|---|---|
| 2004/0167619 A1 | 8/2004 | Case et al. |
| 2004/0181236 A1* | 9/2004 | Eidenschink ............ A61F 2/86 606/108 |
| 2004/0204750 A1 | 10/2004 | Dinh |
| 2004/0220662 A1 | 11/2004 | Dang et al. |
| 2004/0236428 A1 | 11/2004 | Burkinshaw et al. |
| 2005/0004653 A1 | 1/2005 | Gerberding et al. |
| 2005/0004663 A1 | 1/2005 | Llanos et al. |
| 2005/0015138 A1 | 1/2005 | Schuessler et al. |
| 2005/0021131 A1 | 1/2005 | Venkatraman et al. |
| 2005/0060025 A1 | 3/2005 | Mackiewicz et al. |
| 2005/0087520 A1 | 4/2005 | Wang et al. |
| 2005/0107865 A1 | 5/2005 | Clifford et al. |
| 2005/0111500 A1 | 5/2005 | Harter et al. |
| 2005/0147647 A1 | 7/2005 | Glauser et al. |
| 2005/0154450 A1 | 7/2005 | Larson et al. |
| 2005/0157382 A1 | 7/2005 | Kafka et al. |
| 2005/0172471 A1 | 8/2005 | Vietmeier |
| 2005/0211680 A1 | 9/2005 | Li et al. |
| 2005/0222673 A1 | 10/2005 | Nicholas |
| 2005/0234336 A1* | 10/2005 | Beckman ................. A61L 31/18 600/431 |
| 2005/0283226 A1 | 12/2005 | Haverkost |
| 2005/0283228 A1 | 12/2005 | Stanford |
| 2006/0025847 A1 | 2/2006 | Parker |
| 2006/0033240 A1 | 2/2006 | Weber et al. |
| 2006/0120418 A1 | 6/2006 | Harter et al. |
| 2006/0173528 A1 | 8/2006 | Feld et al. |
| 2006/0195175 A1* | 8/2006 | Bregulla ................. A61F 2/915 623/1.15 |
| 2006/0204556 A1* | 9/2006 | Daniels ..................... A61F 2/82 424/443 |
| 2006/0241741 A1 | 10/2006 | Lootz |
| 2007/0021834 A1* | 1/2007 | Young ...................... A61F 2/91 623/16.11 |
| 2007/0038290 A1 | 2/2007 | Huang et al. |
| 2007/0156230 A1* | 7/2007 | Dugan ...................... A61F 2/91 623/1.16 |
| 2007/0179610 A1* | 8/2007 | Biedermann ............. A61F 2/44 623/16.11 |
| 2007/0195006 A1* | 8/2007 | Frye ...................... H01Q 1/1221 343/880 |
| 2007/0266542 A1 | 11/2007 | Melsheimer |
| 2007/0276476 A1 | 11/2007 | Llanos et al. |
| 2007/0293938 A1 | 12/2007 | Gale et al. |
| 2008/0009938 A1* | 1/2008 | Huang ...................... A61F 2/91 623/1.38 |
| 2008/0015684 A1 | 1/2008 | Wu |
| 2008/0033532 A1 | 2/2008 | Dave |
| 2008/0051868 A1* | 2/2008 | Cottone .................... A61F 2/91 623/1.11 |
| 2008/0051873 A1* | 2/2008 | Cottone .................... A61F 2/91 623/1.16 |
| 2008/0132989 A1* | 6/2008 | Snow ....................... A61F 2/95 623/1.12 |
| 2008/0188924 A1 | 8/2008 | Prabhu |
| 2008/0199510 A1* | 8/2008 | Ruane ..................... A61F 2/12 424/426 |
| 2008/0243226 A1 | 10/2008 | Fernandez et al. |
| 2009/0076594 A1 | 3/2009 | Sabaria |
| 2009/0105761 A1* | 4/2009 | Robie ................. A61B 17/1671 606/246 |
| 2009/0112207 A1* | 4/2009 | Walker ............... A61B 17/7016 606/57 |
| 2009/0204203 A1 | 8/2009 | Allen et al. |
| 2010/0004735 A1* | 1/2010 | Yang ........................ A61F 2/91 623/1.16 |
| 2010/0042215 A1* | 2/2010 | Stalcup .................. A61B 17/68 623/16.11 |
| 2010/0094405 A1* | 4/2010 | Cottone .................... A61F 2/91 623/1.16 |
| 2011/0012280 A1* | 1/2011 | Deslauriers ............ A61F 2/4465 264/45.7 |
| 2011/0015743 A1* | 1/2011 | Deslauriers ............ A61F 2/4455 623/17.16 |
| 2011/0130521 A1 | 6/2011 | Thatcher et al. |
| 2011/0130822 A1* | 6/2011 | Cottone .................... A61F 2/91 623/1.15 |
| 2011/0190872 A1* | 8/2011 | Anukhin ................... A61F 2/82 623/1.16 |
| 2011/0208190 A1* | 8/2011 | Kumbar ............... A61B 17/866 606/70 |
| 2011/0238156 A1 | 9/2011 | Tischler et al. |
| 2011/0282428 A1 | 11/2011 | Meyer et al. |
| 2012/0042501 A1 | 2/2012 | Wang et al. |
| 2012/0089219 A1 | 4/2012 | Fircho et al. |
| 2012/0271361 A1* | 10/2012 | Zhou .................... A61B 17/866 606/304 |
| 2013/0131780 A1* | 5/2013 | Armstrong ................ A61F 2/07 623/1.13 |
| 2013/0150943 A1 | 6/2013 | Zheng et al. |
| 2013/0255853 A1 | 10/2013 | Wang et al. |
| 2013/0325104 A1 | 12/2013 | Wu |
| 2013/0325105 A1 | 12/2013 | Wu |
| 2013/0325107 A1 | 12/2013 | Wu |
| 2013/0331926 A1 | 12/2013 | Wu |
| 2013/0331927 A1* | 12/2013 | Zheng ...................... A61F 2/82 623/1.19 |
| 2014/0128901 A1* | 5/2014 | Kang ................. A61B 17/12113 606/194 |
| 2014/0364935 A1* | 12/2014 | Eli .......................... A61F 2/91 623/1.12 |
| 2016/0120671 A1 | 5/2016 | Higashi et al. |
| 2016/0228267 A1* | 8/2016 | Pacetti .................... A61F 2/82 |
| 2016/0242851 A1* | 8/2016 | Lumauig .................. A61F 2/82 |
| 2016/0361182 A1* | 12/2016 | Lumauig ................ A61F 2/915 |
| 2017/0071764 A1 | 3/2017 | Dugan et al. |
| 2017/0333233 A1* | 11/2017 | Lumauig ................ B21J 15/02 |

FOREIGN PATENT DOCUMENTS

| | | |
|---|---|---|
| DE | 197 31 021 | 1/1999 |
| DE | 198 56 983 | 12/1999 |
| DE | 297 24 852 | 2/2005 |
| DE | 103 61 942 | 7/2005 |
| DE | 10 2004 04599 | 3/2006 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 583 170 | 2/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 714 641 | 6/1996 |
| EP | 0 842 729 | 5/1998 |
| EP | 0 970 711 | 1/2000 |
| EP | 1 210 922 | 6/2002 |
| EP | 1 277 449 | 1/2003 |
| EP | 1 479 358 | 11/2004 |
| EP | 1 570 808 | 9/2005 |
| EP | 1 591 079 | 11/2005 |
| EP | 1 656 905 | 5/2006 |
| EP | 2438891 A1 | 4/2012 |
| EP | 2752173 A1 | 7/2014 |
| GB | 2 247 696 | 3/1992 |
| JP | 04-033791 | 2/1992 |
| JP | 07-124766 | 5/1995 |
| JP | 10-166156 | 6/1998 |
| JP | 2002-233578 | 8/2002 |
| JP | 2003-053577 | 2/2003 |
| WO | WO 89/03232 | 4/1989 |
| WO | WO 90/01969 | 3/1990 |
| WO | WO 90/04982 | 5/1990 |
| WO | WO 90/06094 | 6/1990 |

(56) References Cited

FOREIGN PATENT DOCUMENTS

| WO | WO 91/17744 | 11/1991 |
|---|---|---|
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/27587 | 10/1995 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/20429 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 02/26162 | 4/2002 |
| WO | WO 02/38325 | 5/2002 |
| WO | WO 03/015664 | 2/2003 |
| WO | WO 03/015978 | 2/2003 |
| WO | WO 03/047463 | 6/2003 |
| WO | WO 03/057075 | 7/2003 |
| WO | WO 2004/019820 | 3/2004 |
| WO | WO 2004/023985 | 3/2004 |
| WO | WO 2004/062533 | 7/2004 |
| WO | WO 2004/112863 | 12/2004 |
| WO | WO 2005/023480 | 3/2005 |
| WO | WO 2007/081551 | 7/2007 |
| WO | WO 2008/005524 | 1/2008 |
| WO | WO 2014/064180 A1 | 5/2014 |
| WO | WO 2014/181713 A1 | 11/2014 |

OTHER PUBLICATIONS

Acquarulo et al., *Enhancing Medical Device Performance with Nanocomposite Poly*, Med. Device Link, www.devicelink.com/grabber.php3?URL downloaded Mar. 26 2007, 4 pgs.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23(4), pp. 242-243 (1978).
Bull, *Parylene Coating for Medical Applications*, Medical Product Manufacturing News 18, 1 pg. (Mar. 1993).
Casper et al., *Fiber-Reinforced Absorbable Composite for Orthopedic Surgery*, Polymeric Materials Science and Engineering, vol. 53 pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504(Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Eidelman et al., *Characterization of Combinatorial Polymer Blend Composition Gradients by FTIR Microspectroscopy*, J. Res. Natl. Inst. Standards and Technol., vol. 109, No. 2, pp. 219-231 (2004).
Elbert et al., *Conjugate Addition Reactions Combined with Free-Radical Cross-Linking for the Design of Materials for Tissue Engineering*, Biomacromolecules, vol. 2, pp. 430-441 (2001).
Fan et al., *Plasma Absorption of Femtosecond Laser Pulses in Dielectrics*, J. of Heat Transfer, vol. 124, pp. 275-283 (2002).
Hahn et al., *Biacompatibility of Glow-Discharge-Polymerized Films and Vacuum-Deposited Parylene*, J Applied Polymer Sci, vol. 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Hoffnagle et al., *Design and performance of a refractive optical system that converts a Gaussian to a flattop beam*, Applied Optics, vol. 39, No. 30 pp. 5488-5499 (2000).
Kelley et al., *Totally Resorbable High-Strength Composite Material*, Advances in Biomedical Polymers, vol. 35, pp. 75-85 (1987).
Kubies et al., *Microdomain Structure in polylactide-block-poly(ethylene oxide) copolymer films*, Biomaterials, vol. 21, pp. 529-536 (2000).
Kutryk et al., *Coronary Stenting: Current Perspectives*, a companion to the Handbook of Coronary Stents, pp. 1-16 (1999).
Martin et al., *Enhancing the biological activity of immobilized osteopontin using a type-1 collagen affinity coating*, J. Biomed. Mater. Res., vol. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty; Endovascular Stents*, Coron. Arter. Dis., vol. 1(4), pp. 438-448 (Jul./Aug. 1990).
Nichols et al., *Electrical Insulation of Implantable Devices by Composite Polymer Coatings*, ISA Transactions, vol. 26(4), pp. 15-18 (1987).
Peuster et al., *A novel approach to temporary stenting: degradable cardiovascular stents produced from corrodible metal-results 6-18 months after implantation into New Zealand white rabbits*, Heart, vol. 86, pp. 563-569 (2001).
Pietrzak et al., *Bioabsorbable Fixation Devices: Status for the Croniomaxillofacial Surgeon*, J. Craniofaxial Surg., vol. 2, pp. 92-96 (1997).
Pietrzak et al., *Bioresorbable implants—practical considerations*, Bone, vol. 19, No. 1, Supplement Jul. 1996, pp. 1095-1195.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, vol. 79(2), pp. 445-457 (Feb. 1989).
Schmidt et al., *Long-Term implants of Parylene-C Coated Microelectrodes*, Med & Biol Eng & Comp, vol. 26(1), pp. 96-101 (Jan. 1988).
Spagnuolo et al., *Gas 1 is induced by VE-cadherin and vascular endothelial growth factor and inhibits endothelial cell apoptosis*, Blood, vol. 103, pp. 3005-3012 (2004).
Sun et al., *Inert gas beam delivery for ultrafast laser micromachining at ambient pressure*, Am. Inst. of Physics, 6 pgs.
Tamai et al., *Initial and 6-Month Results of Biodegradable Poly-I-Lactic Acid Coronary Stents in Humans*, Circulation, pp. 399-404 (Jul. 25, 2000).
Tsuji et al., *Biodegradable Polymeric Stents*, Current Interventional Cardiology Reports, vol. 3, pp. 10-17 (2001).
Völkel et al., *Targeting of immunoliposomes to endothelial cells using a single-chain Fv fragment directed against human endoglin (CD105)*, Biochimica et Biophysica Acta 1663, pp. 158-166 (2004).
Von Recum et al., *Degradation of polydispersed poly(L-lactic acid) to modulate lactic acid release*, Biomaterials, vol. 16, pp. 441-445 (1995).
Yau et al., *Modern Size-Exclusion Liquid Chromatography*, Wiley-Interscience Publication, IX-XV (1979).

(56) References Cited

OTHER PUBLICATIONS

Zhang et al., *Single-element laser beam shaper for uniform flat-top profiles*, Optics Express, vol. 11, No. 16, pp. 1942-4948 (2003).
International Search Report and Written Opinion dated Jun. 15, 2007 in International Patent Application No. PCT/US2006/049269, 19 pages.
International Search Report and Written Opinion dated Dec. 4, 2007 in International Patent Application No. PCT/US2007/015561, 10 pages.
Office Action dated Mar. 31, 2011 in European Patent Application No. 06848153.0, 4 pages.
Office Action dated Aug. 16, 2011 in Japanese Patent Application No. P2008-549504, 6 pages.
Office Action dated Mar. 27, 2012 in Japanese Patent Application No. P2008-549504, 6 pages.
Extended European Search Report dated Jun. 3, 2014 in European Patent Application No. 13161281.4, 9 pages.
Office Action dated Jun. 22, 2015 in European Patent Application No. 14200352.4, 7 pages.
Extended European Search Report dated Jan. 31, 2017 in European Patent Application No. 16177926.9, 7 pages.

\* cited by examiner

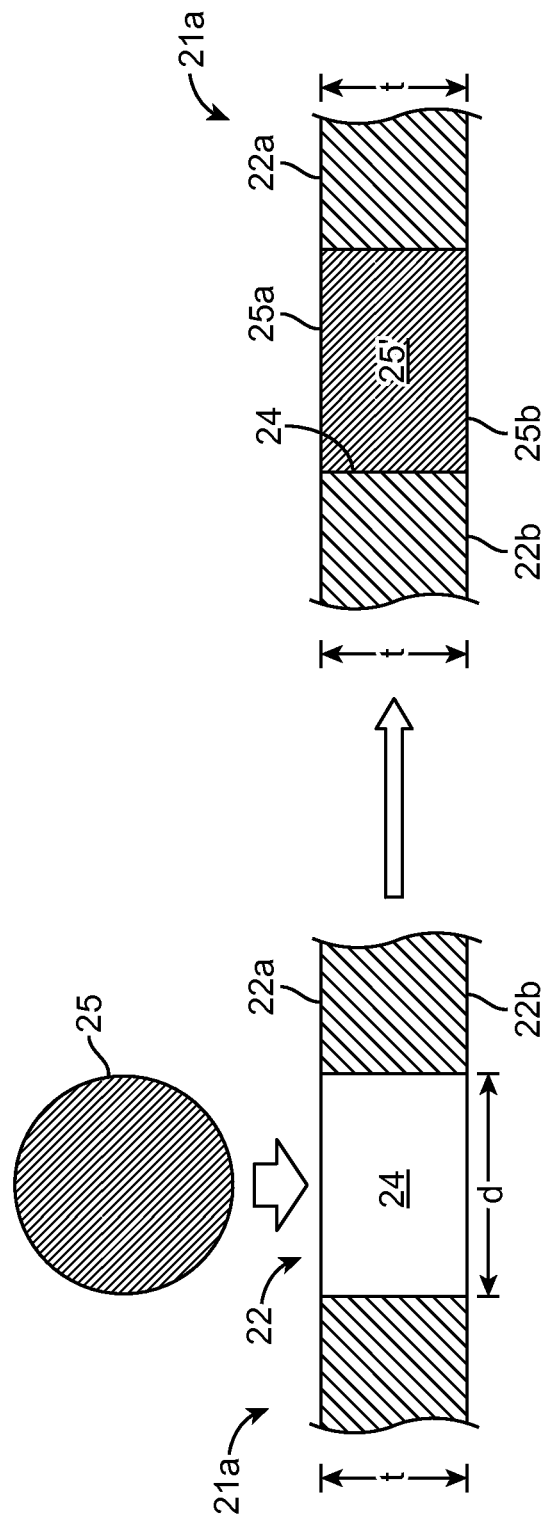

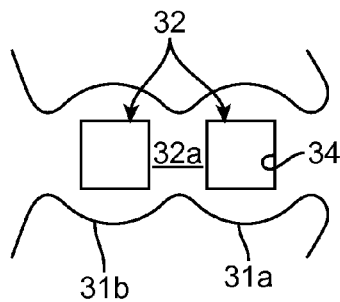
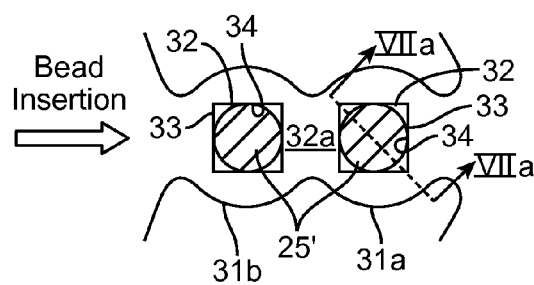
FIG. 4A   FIG. 4B
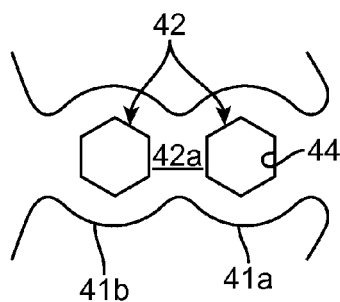
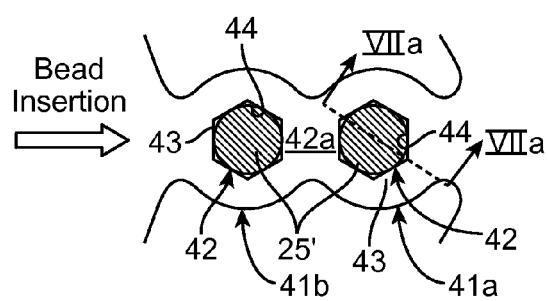
FIG. 5A   FIG. 5B
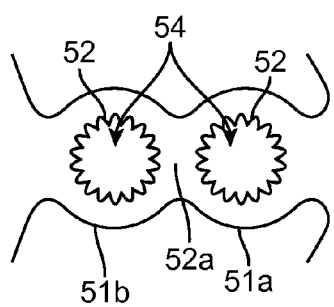
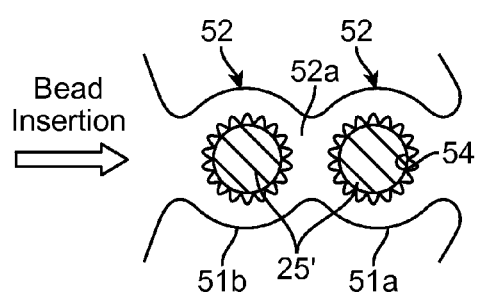
FIG. 6A   FIG. 6B

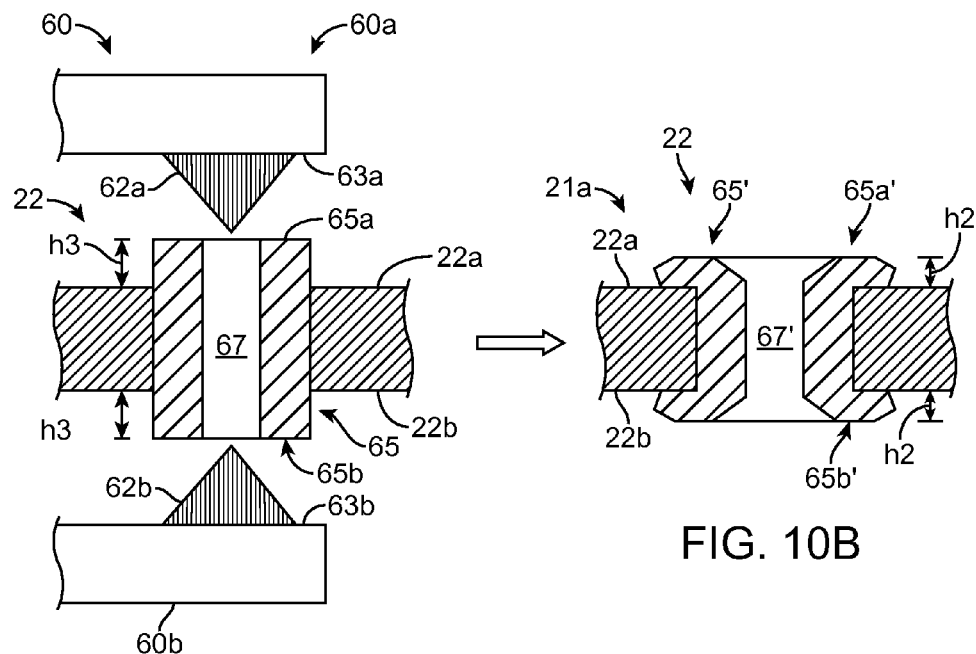
FIG. 10A
FIG. 10B
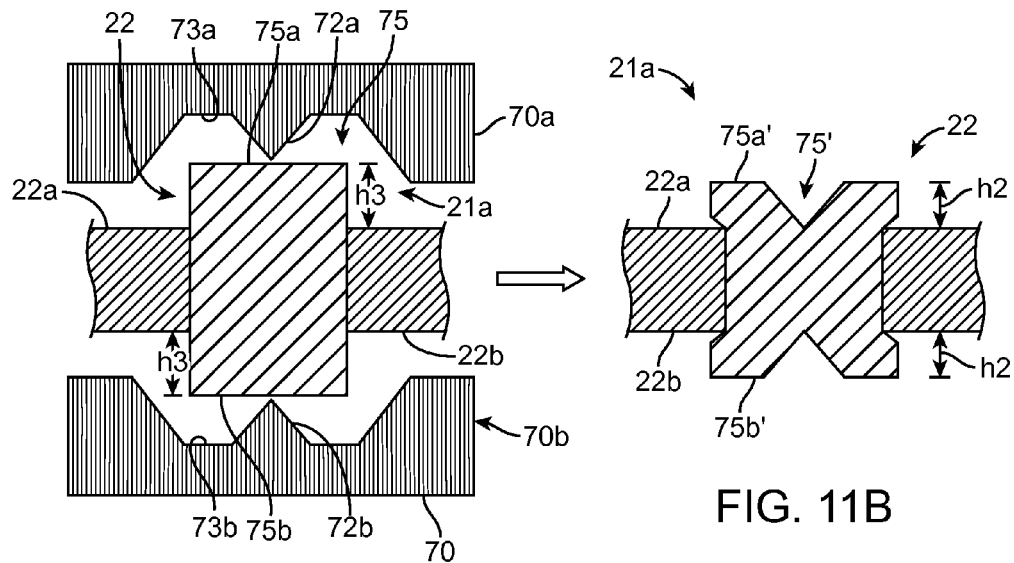
FIG. 11A
FIG. 11B

SCAFFOLDS HAVING RADIOPAQUE MARKERS

BACKGROUND OF THE INVENTION

Field of the Invention

The present invention relates to bioresorbable scaffolds; more particularly, this invention relates to bioresorbable scaffolds for treating an anatomical lumen of the body.

Description of the State of the Art

Radially expandable endoprostheses are artificial devices adapted to be implanted in an anatomical lumen. An "anatomical lumen" refers to a cavity, or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer, or other resorbable material such as an erodible metal, and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

Examples of bioresorbable polymer scaffolds include those described in U.S. Pat. No. 8,002,817 to Limon, U.S. Pat. No. 8,303,644 to Lord, and U.S. Pat. No. 8,388,673 to Yang. FIG. 1 shows a distal region of a bioresorbable polymer scaffold designed for delivery through anatomical lumen using a catheter and plastically expanded using a balloon. The scaffold has a cylindrical shape having a central axis 2 and includes a pattern of interconnecting structural elements, which will be called bar arms or struts 4. Axis 2 extends through the center of the cylindrical shape formed by the struts 4. The stresses involved during compression and deployment are generally distributed throughout the struts 4 but are focused at the bending elements, crowns or strut junctions. Struts 4 include a series of ring struts 6 that are connected to each other at crowns 8. Ring struts 6 and crowns 8 form sinusoidal rings 5. Rings 5 are arranged longitudinally and centered on an axis 2. Struts 4 also include link struts 9 that connect rings 5 to each other. Rings 5 and link struts 9 collectively form a tubular scaffold 10 having axis 2 represent a bore or longitudinal axis of the scaffold 10. Ring 5d is located at a distal end of the scaffold. Crown 8 form smaller angles when the scaffold 10 is crimped to a balloon and larger angles when plastically expanded by the balloon. After deployment, the scaffold is subjected to static and cyclic compressive loads from surrounding tissue. Rings 5 are configured to maintain the scaffold's radially expanded state after deployment.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. Scaffolds may also be constructed of bioerodible metals and alloys. The scaffold, as opposed to a durable metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(D,L-lactide-co-glycolide) ("PLGA"), poly(D-lactide-co-glycolide) or poly(L-lactide-co-D-lactide) ("PLLA-co-PDLA") with less than 10% D-lactide, poly(L-lactide-co-caprolactone), poly (caprolactone), PLLD/PDLA stereo complex, and blends of the aforementioned polymers may be described, through comparison with a metallic material used to form a stent, in some of the following ways. Polymeric materials typically possess a lower strength to volume ratio compared to metals, which means more material is needed to provide an equivalent mechanical property. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymers such as PLLA or PLGA.

One additional challenge with using a bioresorbable polymer (and polymers generally composed of carbon, hydrogen, oxygen, and nitrogen) for a scaffold structure is that the material is radiolucent with no radiopacity. Bioresorbable polymers tend to have x-ray absorption similar to body tissue. A known way to address the problem is to attach radiopaque markers to structural elements of the scaffold, such as a strut, bar arm or link. For example, FIG. 1 shows a link element 9d connecting a distal end ring 5d to an adjacent ring 5. The link element 9d has a pair of holes. Each of the holes holds a radiopaque marker 11. There are challenges to the use of the markers 11 with the scaffold 10.

There needs to be a reliable way of attaching the markers 11 to the link element 9d so that the markers 11 will not separate from the scaffold during a processing step like crimping the scaffold to a balloon or when the scaffold is balloon-expanded from the crimped state. These two events—crimping and balloon expansion—are particularly problematic for marker adherence to the scaffold because both events induce significant plastic deformation in the scaffold body. If this deformation causes significant out of plane or irregular deformation of struts supporting, or near to markers the marker can dislodge (e.g., if the strut holding the marker is twisted or bent during crimping the marker can fall out of its hole). A scaffold with radiopaque markers and methods for attaching the marker to a scaffold body is discussed in US20070156230.

There is a continuing need to improve upon the reliability of radiopaque marker securement to a scaffold; and there is also a need to improve upon methods of attaching radiopaque markers to meet demands for scaffold patterns or structure that render prior methods of marker attachment in adequate or unreliable.

SUMMARY OF THE INVENTION

What is disclosed are scaffolds having radiopaque markers and methods for attaching radiopaque markers to a strut, link or bar arm of a polymeric scaffold.

According to one aspect markers are re-shaped to facilitate a better retention within a marker hole. Examples include a marker shaped as a tube or rivet.

According to another aspect a hole for retaining the marker is re-shaped to better secure the marker in the hole. Examples include holes having polygonal shapes or holes having grooves.

According to another aspect of the invention a scaffold structure for holding a marker and method for making the same addresses a need to maintain a low profile for struts exposed in the bloodstream, while ensuring the marker will be securely held in the strut. Low profiles for struts mean thinner struts or thinner portions of struts. The desire for low profiles addresses the degree thrombogenicity of the scaffold, which can be influenced by a strut thickness overall and/or protrusion from a strut surface. Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. Low strut profile also leads to less neointimal proliferation as the neointima will proliferate to the degree necessary to cover the strut. As such coverage is a necessary step to complete healing. Thinner struts are believed to endothelialize and heal more rapidly.

Markers attached to a scaffold having thinner struts, however, may not hold as reliably as a scaffold having thicker struts since there is less surface contact area between the strut and marker. Embodiments of invention address this need. According to another aspect a thickness of the marker and strut is kept below threshold values while reliably retaining the marker in the hole.

According to other aspects of the invention, there is a scaffold, medical device, method for making such a scaffold, method of attaching a marker to a strut or bar arm of a scaffold, or method for assembly of a medical device comprising such a scaffold having one or more, or any combination of the following things (1) through (19):

(1) A method to reduce the thrombogenicity, or a scaffold having reduced thrombogenicity, the scaffold comprising a strut, the strut including a strut thickness and a marker attached to the strut, wherein the strut has a thickness (t) and the marker has a length (L, as measured from abluminal to luminal surface portions) and is held in the strut, the marker including a portion that can protrude outward from an abluminal and/or luminal surface of the strut, wherein the marker length (L) and strut/link/bar arm thickness (t) are related as follows: $1.2 \le (L/t) \le 1.8$; $1.1 \le (L'/t) \le 1.5$; $1.0 \le (L/t) \le 1.8$; and/or $1.0 \le (L'/t) \le 1.5$, where L is an undeformed length (e.g., rivet, tube), L' is a deformed length (e.g. a rivet, coating or snap-in marker between abluminal and luminal surfaces).

(2) A scaffold comprising a bar arm, link or strut having a hole holding a marker, or a method for making the same according to one or more, or any combination of features described for a Concept A through Concept G infra and with reference to illustrative examples shown in FIGS. 3A-3C, FIGS. 4A, 4B, 5A and 5B, FIGS. 6A and 6B, FIG. 6C, FIGS. 7A-7B, FIGS. 8A-8C, FIGS.

9A-9C, FIGS. 10A-10B, FIGS. 11A-11B, FIGS. 12A-12B and FIGS. 13A-13B, respectively.

(3) An aspect ratio (AR) of strut width (w) to wall thickness (t) (AR=w/t) is between 0.5 to 2.0, 0.5 to 1.5, 0.7 to 1.5, 0.7 to 1.3, 0.9 to 1.5, 0.9 to 1.2, 1.0 to 1.5, 1.5 to 2.0, or 2.0 to 3.0;

(4) A scaffold comprising a strut, link and/or bar arm including a marker secured to the strut, link and/or bar arm according to any of Concept A, Concept B, Concept C, Concept D, Concept E, Concept F or Concept G—type markers.

(5) A scaffold comprising a deformed marker secured to a strut, bar arm and/or link, wherein the marker is a rivet, snap-fit, irregularly-shaped, tube or spherical marker before the marker is deformed.

(6) A marker having a head and a tail such as a rivet, hollow tube, solid tube, polygonal, oblate spheroid, and/or spherical body. The marker is secured to a strut, bar arm, link and/or connector.

(7) A combined bump (luminal side plus abluminal side, and referring to a portion of a marker and/or polymer at the marker) is no more than a strut or link thickness, e.g., no more than 100 or 85 microns, so that the length at the marker is at most twice a strut or bar arm thickness at the marker.

(8) A combined bump (luminal side plus abluminal side, and referring to a portion of a marker and/or polymer at the marker) is at least 10-50% more than a thickness of a strut or bar arm at the marker.

(9) A wall thickness for a scaffold (pre-crimp diameter of 3 to 5 mm) is less than 150 microns, less than 140 microns, less than 130 microns, about 100 micron, 80 to 100 microns, 80 to 120 microns, 90 to 100 microns, 90 to 110 microns, 110 to 120 microns, or 95 to 105 microns. More preferably a wall thickness is between 80 and 100 microns, and more preferably between 85 and 95 microns; and

(10) A wall thickness for a scaffold (pre-crimp diameter of 7 to 10 mm) is less than 280 microns, less than 260 microns, less than 240 microns, about 190 micron, 149 to 186 microns, 149 to 220 microns, 170 to 190 microns, 170 to 210 microns, 210 to 220 microns. More preferably a wall thickness is between 150 and 190 microns for a scaffold having an outer diameter of 7, 8 or 9 mm.

(11) A polymeric scaffold is heated about 0-20 degrees above its Tg during or after marker placement.

(12) The radiopaque marker is comprised of platinum, platinum/iridium alloy, iridium, tantalum, palladium, tungsten, niobium, zirconium, iron, zinc, magnesium, manganese or their alloys.

(13) A method for making a medical device, comprising: providing a polymer scaffold including a strut having a hole formed in the strut, wherein the hole has a length and a width; and providing a radiopaque marker having a first end, second end, and medial portions; and attaching the marker to the scaffold including placing the marker into the hole; wherein when the marker is attached to the scaffold the medial portion is disposed in the hole and the marker is retained in the hole at least partially by one or both of the first and second ends.

(14) The method of (6) according to one or more, or any combination of the following things: wherein the attaching step includes deforming at least one of the first and second ends such that the deformed end has a width greater than the hole width; wherein the marker is a rivet having a head and tail, and wherein the tail is the deformed end; wherein the rivet head is placed on a luminal side of the strut and held in place by a mandrel, and the tail disposed on the abluminal strut side is deformed by a roller or pin; wherein the marker is a tube and both the first and second ends are deformed to have a width greater than the hole width; wherein the attaching step includes using a tool having jaws forming points to engage the tube ends, wherein the jaws deform the ends; wherein the marker is a snap-fit marker; wherein the marker has an undeformed length (L), a deformed length (L'), and the strut has a thickness (t), and the marker lengths and strut thickness are related as follows: $1.2 \leq (L/t) \leq 1.8$; $1.1 \leq (L'/t) \leq 1.5$; and/or wherein the marker has an undeformed length (L), a deformed length (L'), and the strut has a thickness (t), and the marker lengths and strut thickness are related as follows: $1.0 \leq (L/t) \leq 1.8$; and $1.0 \leq (L'/t) \leq 1.5$.

(15) A method for making a medical device, comprising: providing a polymer scaffold including a strut; making a grooved hole in the strut including forming at least one groove in a wall of the hole; and attaching a radiopaque marker to the scaffold including placing the marker into the grooved hole.

(16) The method of (8) according to one or more, or any combination of the following things: wherein the grooved hole has vertical grooves extending generally parallel to a bore axis of the hole; wherein the grooved hole has one or more spiral grooves; wherein the grooved hole is a tapped hole having between about 2 to 6 threads per 100 microns; wherein the grooved hole is an annular hole disposed between upper and lower rims of the hole; wherein the making the grooved hole includes using a laser and reflector to etch the annular hole; wherein the hole is polygonal hole; wherein the hole elliptical; further comprising applying a polymer melt or coating to the hole and marker, whereby the polymer becomes disposed between gaps between the at least one groove and marker.

(17) A method, comprising: providing a scaffold made from a polymer tube, the scaffold having a network of elements including a strut; providing a hole in the strut or link, wherein the hole extends from an abluminal surface to a luminal surface of the strut; disposing a radiopaque marker at least partially within the hole; and applying a coating comprising a polymer to the luminal and abluminal surfaces; wherein a thickness measured between abluminal and luminal surfaces of the coating nearby to the marker (tc) is related to a length (L) measured between abluminal and luminal surfaces of the coating at the marker as $0.8 \leq (L/tc) \leq 1.8$.

(18) The method of (10) according to one or more, or any combination of the following things: wherein t is about 100 microns; and/or wherein the marker height (L), the marker is secured to a strut, the strut thickness is t, and $1.1 \leq (L/t) \leq 1.5$.

(19) A medical device, comprising: a scaffold made from a polymer tube, the scaffold having a network of elements including a strut or link; a hole formed in the strut or link, wherein the hole extends from the abluminal surface to the luminal surface; a radiopaque marker at least partially disposed within the hole; and a coating comprising a polymer on the luminal and abluminal surfaces; wherein a thickness measured between abluminal and luminal surfaces of the coating adjacent the marker (tc) is related to a length (L) measured between abluminal and luminal surfaces of the coating at the marker as $1.1 \leq (L/tc) \leq 1.5$.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 2A is a partial side-cross sectional view of the link of FIG. 2 taken at section IIA-IIA with a spherical marker being placed in the hole.

FIG. 2B shows the link of FIG. 2A after the marker is placed in the hole.

FIG. 4A is a top view of a polygonal, four-sided marker hole without an inserted marker.

FIG. 4B is a top view of the polygonal, four-sided marker hole of FIG. 4A with an inserted marker.

FIG. 5A is a top view of a polygonal, six-sided marker hole without an inserted marker.

FIG. 5B is a top view of the polygonal, six-sided marker hole of FIG. 5A with an inserted marker.

FIG. 6A is a top view of a marker hole with grooves, without an inserted marker.

FIG. 6B is a top view of the marker hole of FIG. 6A, with an inserted marker.

FIG. 7A shows the marker hole and marker without a polymer coating.

FIG. 7B shows the marker hole and marker with a polymer coating.

FIGS. 10A and 10B are cross-sectional views of a link and marker and method of attaching the marker to the link according to another embodiment.

FIGS. 11A and 11B are cross-sectional views of a link and marker and method of attaching the marker to the link according to another embodiment.

DETAILED DESCRIPTION

Figure 1:
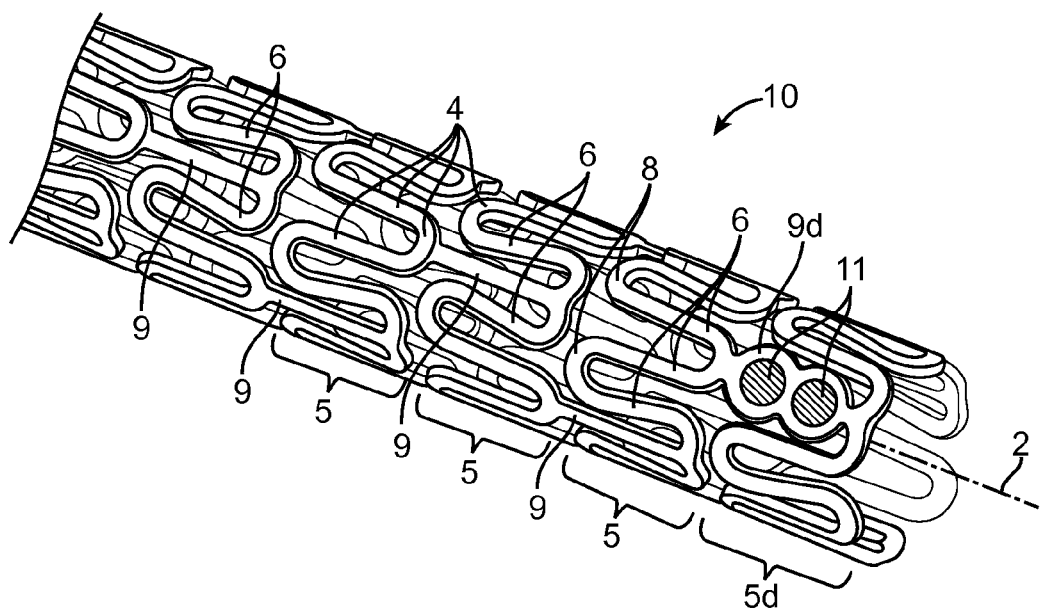
FIG. 1 is a perspective view of a portion of a prior art scaffold. The scaffold is shown in a crimped state (balloon not shown).

In the description like reference numbers appearing in the drawings and description designate corresponding or like elements among the different views.

For purposes of this disclosure, the following terms and definitions apply:

The terms "about," "approximately," "generally," or "substantially" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance or standard deviation from d1.

It is understood that any numerical value, range, or either range endpoint (including, e.g., "approximately none", "about none", "about all", etc.) preceded by the word "about," "approximately," "generally," or "substantially" in this disclosure also describes or discloses the same numerical value, range, or either range endpoint not preceded by the word "about," "approximately," "generally," or "substantially."

A "stent" means a permanent, durable or non-degrading structure, usually comprised of a non-degrading metal or metal alloy structure, generally speaking, while a "scaffold" means a temporary structure comprising a bioresorbable or biodegradable polymer, metal, alloy or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the inner diameter or the outer diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon (i.e., a balloon having a 6.5 mm nominal diameter when inflated to a nominal balloon pressure such as 6 times atmospheric pressure) has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

When reference is made to a diameter it shall mean the inner diameter or the outer diameter, unless stated or implied otherwise given the context of the description.

When reference is made to a scaffold strut, it also applies to a link or bar arm.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "pre-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

Bioresorbable scaffolds comprised of biodegradable polyester polymers are radiolucent. In order to provide for fluoroscopic visualization, radiopaque markers are placed on the scaffold. For example, the scaffold described in U.S. Pat. No. 8,388,673 ('673 patent) has two platinum markers 206 secured at each end of the scaffold 200, as shown in FIG. 2 of the '673 patent.

Figure 2:
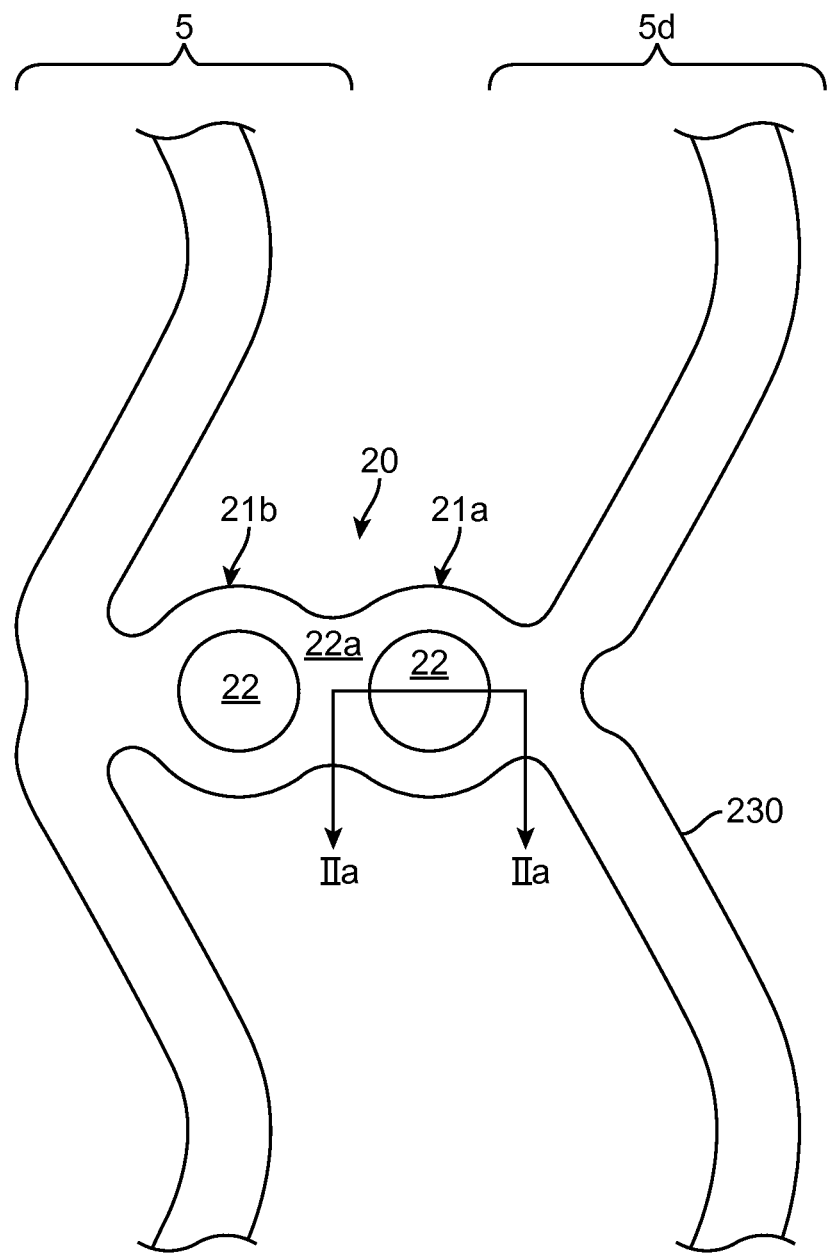
FIG. 2 is a top partial view of a scaffold showing a link connecting adjacent rings. The link includes holes for holding markers.

FIG. 2 is a top planar view of a portion of a polymer scaffold, e.g., a polymer scaffold having a pattern of rings interconnected by links as in the case of the '673 patent embodiments. There is a link strut 20 extending between rings 5d, 5 in FIG. 2. The strut 20 has formed left and right structures or strut portions 21b, 21a, respectively, for holding a radiopaque marker. The markers are retainable in holes 22 formed by the structures 21a, 21b. The surface 22a corresponds to an abluminal surface of the scaffold. An example of a corresponding scaffold structure having the link 20 is described in FIGS. 2, 5A-5D, 6A-6E and col. 9, line 3 through col. 14, line 17 of the '673 patent. The embodiments of a scaffold having a marker-holding link structure or method for making the same according to this disclosure in some embodiments include the embodiments of a scaffold pattern according to FIGS. 2, 5A-5D, 6A-6E and col. 9, line 3 through col. 14, line 17 of the '673 patent.

One method for marker placement forces a spherical-like body into a cylindrical hole. This process is illustrated by FIGS. 2A and 2B. Shown in cross-section is the hole 22 and surrounding structure of the link portion 21a as seen from Section IIa-IIa in FIG. 2. The hole 22 extends through the entire thickness (t) of the strut portion 21a and the hole 22 has an about constant diameter (d) from the luminal surface 22b to the abluminal surface 22a. A generally spherical marker 25 is force-fit into the hole 22 to produce the marker 25' in the hole 22 illustrated in FIG. 2B. The spherical marker 25 has a volume about equal to, less than or greater than the volume of the open space defined by the plane of the abluminal surface 22a, the plane of the luminal surface 22b and the generally cylindrical walls 24 of the hole 22. The spherical body is reshaped into body 25' by the walls 24 and a tool. The deformed shape 25' may be achieved by using one or two rollers pressed against the sphere 25 when it is disposed within the hole 22. The rollers (not shown) are pressed against each side of the marker 25 to produce the deformed marker 25' structure shown in FIG. 2B. Alternatively, the marker 25 may be held on a tip of a magnetized, or vacuum mandrel and pressed (from the abluminal surface 22a side) into the hole 22 while a non-compliant flat surface is pressed into the marker from the luminal side 22b. Referring to FIG. 2B, the marker 25' has an abluminal surface 25a that is about flush with surface 22a and luminal surface 25b that is about flush with surface 22b. Methods for placing the marker 25 in the hole 22 are discussed in US20070156230.

According to one example, the hole 22 has a hole diameter (d) of 233.7 µm and an average initial spherical marker size (Johnson-Matthey marker beads) of 236.7 µm. The thickness (t) is 157.5 microns and hole 22 volume is $t \times \pi d^2 = 6.76$ E6 µm$^3$. The average spherical volume size is 6.94 E6 µm$^3$. Hence, in this embodiment when the spherical marker 25 is press-fit into the hole 22, the marker 25 is deformed from a generally spherical shape into more of a cylindrical shape. In some embodiments an average volume size for the marker 25 may be only slightly larger in volume (3%) than a hole 22 volume. Larger beads presumably stretch the marker brim while smaller beads will contact the walls 24 when deformed, but do not fill the hole 22 volume completely. As would be understood, the about flush with the luminal and abluminal surfaces accounts for the variances in marker 25 volume size from the manufacturer and volume size variances of the hole 22 volume.

TABLE 1 contains a theoretical volume of an average spherical platinum marker 25 relative to that of the hole 22 for a Scaffold A and a Scaffold B.

TABLE 1

Marker and Hole Dimensions

| Scaffold | Strut Thickness (µm) | Marker Hole Diameter (µm) | Average Marker Diameter (µm) | Idealized Marker Hole Volume (µm$^3$) | Average Marker Volume (µm$^3$) |
|---|---|---|---|---|---|
| A | 157.5 | 233.7 | 236.7 | 6.76E6 | 6.94E6 |
| B | 100 | 241.3 | 236.7 | 4.57E6 | 6.94E6 |

The larger the marker volume is relative to the hole volume, the more the marker brim or space 22 must increase in size if the marker 25' will be flush with the surfaces 22a, 22b. Otherwise, if the volume for the hole 22 does not increase marker material would be left protruding above and/or below the hole 22.

With respect to the different thickness struts of Scaffold A and Scaffold B (TABLE 1) it will be appreciated that an acceptable marker 25 fitting method and/or structure for Scaffold A (thick struts) may not be acceptable for Scaffold B (thin struts). It may be necessary to change the volume and/or shape size of the hole and/or marker, and/or method of attachment of the marker to a hole when a strut thickness is reduced in size, e.g., when there is an about 37% reduction in strut thickness.

There are several dimensional parameters that result in a physical interaction between the strut walls 24 and marker 25 surface sufficient to keep the marker in the hole 25 during scaffold manipulations, such as drug coating, crimping and scaffold expansion.

Factors (1)-(3) that affect the physical securement of the marker 25' in the hole 22 include:
  (1) The interference fit between the marker 25' and the inside surface or brim 24 of the marker hole 22. This fit is a function of
    The total contact area between the marker 25' and the polymer walls or brim 24.
    The residual stresses in the marker brim 24 polymer and 25' that results in a compressive or hoop stress between the marker brim 24 and marker 25'.
  (2) The roughness of the marker 25' surface and surface of the brim 24, or coefficient of static friction between the contacting marker and wall surfaces.
  (3) Where a drug-polymer coating is applied (not shown in FIG. 2B), the gluing-in effect of the drug/polymer coating. The contribution of this coating to marker 25' retention comes down to the fracture strength of the coating on the abluminal or luminal surfaces 22a, 22b as the coating must fracture through its thickness on either side for the marker 25' to become dislodged.

With respect to factor (3), in some embodiments an Everolimus/PDLLA coating is applied after the marker 25' is fit in place. This type of coating can seal in the marker 25. However, an Everolimus/PDLLA coating tends to be thin (e.g., 3 microns on the abluminal surface 22a and 1 micron on the luminal surface 22b), which limits it's out of plane shear strength resisting dislodgment of the marker from the hole.

In some embodiments a polymer strut, bar arm and/or link has a thickness about, or less than about 100 microns, which is less than the wall thickness for known scaffolds cut from tubes. There are several desirable properties or capabilities that follow from a reduction in wall thickness for a scaffold strut; for example, a reduction from the Scaffold A wall thickness to Scaffold B wall thickness. The advantages of using the reduced wall thickness include a lower profile and hence better deliverability, reduced acute thrombogenicity, and potentially better healing. In some embodiments the Scaffold B (100 micron wall thickness) has a pattern of rings interconnected by struts as disclosed in the '673 patent.

In some embodiments it is desirable to use the same size marker 25 for Scaffold B as with Scaffold A, so that there is no difference, or reduction, in radiopacity between the two scaffold types. Reducing the strut thickness, while keeping the marker hole 22 the same size can however result in the marker protruding above and/or below the strut surfaces due to the reduced hole volume. It may be desirable to keep the abluminal and luminal surfaces 25a, 25b of the marker 25' flush with corresponding surfaces 22a, 22b for Scaffold B, in which case the hole 22 diameter (d) may be increased to partially account for the reduced hole volume resulting from the thinner strut. This is shown in TABLE 1 for Scaffold B, which has a hole diameter greater than the hole diameter for Scaffold A.

With respect to Factor (1) it will be appreciated that the substantially frictional force relied on to resist dislodgement of the marker 25' from the hole 22 reduces as the strut thickness is reduced. When using a fixed sized marker of constant volume, and assuming the marker fills a cylindrical hole, the contact area between the marker and hole sidewall may be expressed in terms of a marker volume and strut thickness, as in EQ. 1.

$$A = 2(\pi t V)^{1/2} \qquad (EQ. 1)$$

Where
A=Contact area between marker hole sidewall and marker
t=Strut thickness
V=marker volume EQ. 1 shows that in a limiting case of the strut 21a thickness becoming very thin (t→0), the marker 25' becomes more and more like a thin disc, which would have minimal mechanical interaction with the wall 24. Hence the frictional forces between the marker 25' and wall 24 decreases because the contact area is reduced. Comparing Scaffold A with Scaffold B, the marker 25' retention force in the hole 22 therefore becomes worse due to the about 37% reduction in strut thickness. Indeed, it may be expected that the Factor A (frictional) forces that hold the marker 25' in the hole reduce by about 20%, which 20% reduction is the surface area reduction of the walls 24 when the strut thickness is reduced by the about 37% (Scaffold A→Scaffold B). This assumes the coefficients of static friction and level of residual hoop stress are otherwise unchanged between Scaffold A and B.

According to another aspect of the disclosure there are embodiments of a strut having a hole for holding a radiopaque marker and methods for securing a marker to a strut. The embodiments address the ongoing need for having a more secure attachment of a marker to a polymer strut. In preferred embodiments the polymer strut has a thickness, or a scaffold comprising the strut is cut from a tube having a wall thickness less than about 160 μm or 150 μm, a wall thickness of about 100 μm or a wall thickness less than 100 μm and while retaining the same size marker as a strut having a thickness between 150-160 μm, so that the radiopacity of the scaffold does not change.

An improved securement of a marker to a hole according to the disclosure includes embodiments having one or more of the following Concepts A through G:
  A. Following marker insertion a sealing biodegradable polymer is applied to secure the marker in place (Concept A).
  B. The strut hole is made in an irregular shape to increase an adhesive and mechanical locking effect of a scaffold coating (Concept B).
  C. The marker has roughened surfaces to increase the coefficient of friction between the polymer walls and marker (Concept C).
  D. The holes are made concave to increase the contact area and/or to provide a mechanical engagement between the marker and the hole (Concept D).
  E. Radiopaque markers shaped like, or usable as rivets are attached to the hole (Concept E).
  F. Polygonal or Irregular markers (Concept F).
  G. Snap-in markers (Concept G).

Figure 3A:
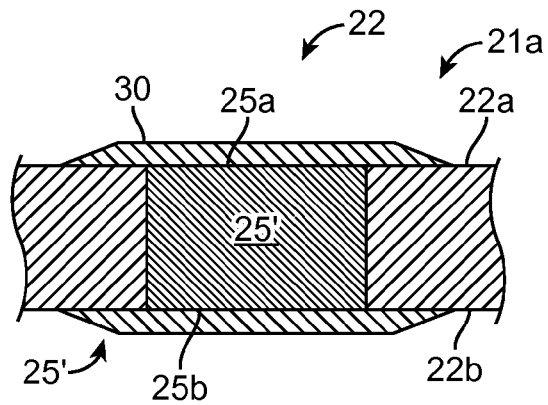
FIG. 3A shows a first embodiment of sealing layers of a polymer applied to abluminal and luminal surfaces of a marker strut.
Figure 3B:
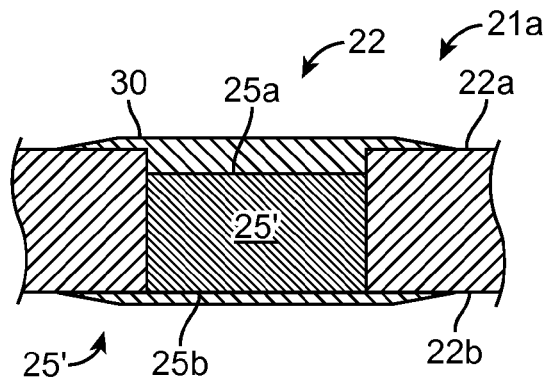
FIG. 3B shows a second embodiment of sealing layers of a polymer applied to abluminal and luminal surfaces of a marker strut.
Figure 3C:
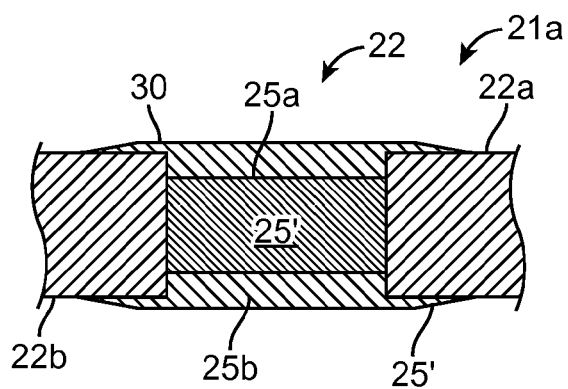
FIG. 3C shows a third embodiment of sealing layers of a polymer applied to abluminal and luminal surfaces of a marker strut.

A. Addition of a Sealing Biodegradable Polymer after Marker Insertion, but Before Drug Spray According to Concept A, sealing layers of polymer 30 are applied to the abluminal and/or luminal surfaces 22a, 22b of the strut 21a near the marker 25' and luminal and abluminal surfaces 25a, 25b surfaces of the marker 25' as shown in FIGS. 3A-3C. The amount of sealing polymer 30 applied on the marker 25 may be significant but without creating an unsatisfactory bump or protrusion on the abluminal or luminal surfaces. To increase the available space for the sealing polymer (without reducing the marker size or creating a large bump on the surface) the hole 22 may be made wider, so that the marker 25 when pressed and deformed into the hole 22 is recessed from the abluminal surface 22*a* and/or abluminal surface 22*b*. This is shown in FIGS. 3B and 3C. In FIG. 3B the marker 25' is recessed from the side 22*a* but flush with 22*b*. In FIG. 3C the marker 25' is recessed on both surfaces.

The sealing polymer 30 may be applied in different ways. One approach is to apply a small amount of solution consisting of a biodegradable polymer dissolved in solvent. This can be done with a fine needle attached to a microsyringe pump dispenser. The solution could be applied to both the abluminal and luminal surfaces of the marker and marker brim portions of the hole 22 (FIGS. 3A-3C). Suitable polymers include poly(L-lactide) ("PLLA"), poly(D,L-lactide-co-glycolide) ("PLGA"), poly(D-lactide-co-glycolide), poly(D,L-lactide) ("PDLLA") poly(L-lactide-co-caprolactone) ("PLLA-PCL") and other bioresorbable polymers. Solvents include chloroform, acetone, trichloroethylene, 2-butanone, cyclopentanone, ethyl acetate, and cyclohexanone.

Alternatively, the sealing polymer may be applied in a molten state. As compared to the solvent application embodiment of the sealing polymer, a polymer applied in the molten state may produce a more sizable bump or protrusion on the abluminal and/or luminal surface 22*a*, 22*b*. While avoidance of bumps on these surfaces is generally of concern, small bumps or protrusions are acceptable if they are less than the strut thickness. For example, in some embodiments the bump is less than about 100 microns, or about 85 microns (combined bumps on luminal and abluminal sides). Thus the length of the marker (L' or L) may be up to about 100 or 85 microns higher than the strut thickness, as in a strut thickness of about 100 or 85 microns.

B. Use of a Polygonal or Irregular Marker Hole to Improve Adhesive Effect of Coating According to Concept B, the marker hole 22 is modified to increase the adhesive effect of a drug/polymer coating on increasing the marker retention. If larger gaps are made between the marker 25 and wall 24 of the hole 22 more of the coating can become disposed between the marker 25' and wall 24 of the hole 22. The presence of the coating in this area (in addition to having coating extending over the surfaces 22*a*, 25*a*, 22*b* and 25*a*) can help to secure the marker 25 in the hole because the surface area contact among the coating, wall 24 and marker 25 is increased. Essentially, the coating disposed within the gaps between the wall 24 and marker 25 can perform more as an adhesive. In addition, the coating filling in around the deformed marker bead can improve retention via mechanical interlocking. Gaps can be made by forming the hole with rectangular, hexagonal or more generally polygonal sides as opposed to a round hole. When a spherical marker 25 is pressed into a hole having these types of walls there will be gaps at each wall corner.

FIGS. 4A and 4B show modified marker-holding strut portions 31*a*, 31*b* before and after, respectively, a marker 25 is pressed into each hole 32 of the strut portions 31*a*, 31 *b*. The holes 32 are formed as rectangular holes. Since there are four sides 34 to a rectangular, there are four corners to the hole 32. As can be appreciated from FIG. 4B there are four gaps 33 between the hole walls 34 and the bead 25'. The gaps 33 are present at each wall corner of the rectangular hole 32.

FIGS. 5A and 5B show modified marker-holding strut portions 41*a*, 41*b* before and after, respectively, a marker 25 is pressed into each hole 42 of the strut portions 41*a*, 41 *b*. The holes 42 are formed as hexagonal holes. Since there are six sides 44 to a hexagon, there are six corners to the hole 42. As can be appreciated from FIG. 5B there is at least one and up to six gaps 43 between the hole walls 44 and the marker 25'.

Figure 7A:
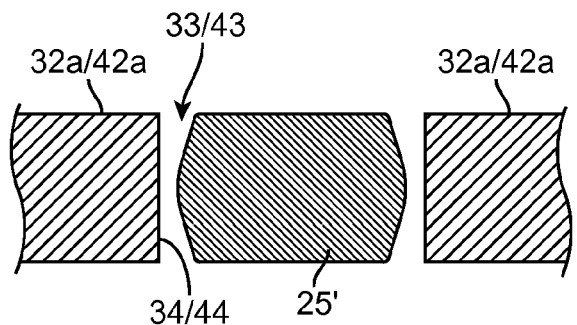
FIG. 7A is a cross sectional view of the marker according to any of the embodiments of FIGS. 4A, 4B, 5A and 5B, where
Figure 7B:
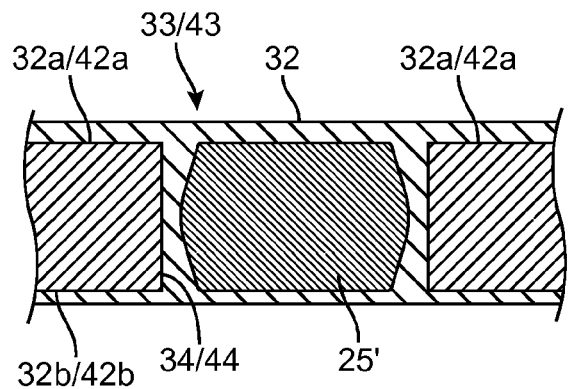
FIG. 7B is a cross sectional view of the marker according to any of the embodiments of FIGS. 4A, 4B, 5A and 5B, where

Referring to FIGS. 7A and 7B there is shown crosssectional side-views of the holes 32 and 42 with the marker 25' in the hole. The view of FIG. 7A is taken from section VIIa-VIIa in FIGS. 4B and 5B. As shown there is the gap 33, 43 present at the corner, which provides space for the polymer coating 32 (FIG. 7B) to lodged when the coating is applied to the scaffold. The coating 32 is disposed between the surface of the marker 25' and wall 34, 44 of the hole 32, 42 combined with the coating disposed on the luminal and/or abluminal surfaces 32*a*, 32*b*, 42*a*, 42*b*. The polymer coating 32 shown in FIG. 7B may be a drug-polymer coating or polymer coating applied by spraying, or a molten polymer applied to the brim of the hole 22 and over the marker 25'.

C. Roughened Wall Surfaces

FIGS. 6A and 6B show modified marker-holding strut portions 51*a*, 51*b* before and after, respectively, a marker 25' is pressed into each hole 52 of the strut portions 51*a*, 51 *b*. The holes 52 are formed as bearclaw holes or holes having grooves 54 formed through the thickness and along the perimeter of the hole. The grooves 54 may be formed using a laser directed down into the hole and moved circumferentially about the perimeter to cut out the grooves 54. Each of the grooves 54 can serve as a gap that fills up with a coating or molten polymer 32 to form an adhesive binding surfaces of the marker 25' to walls of the hole 52, in the same way as the embodiments of FIGS. 4A, 4B, 5A and 5B where the binding occurs at wall corners 33, 43.

Figure 6C:
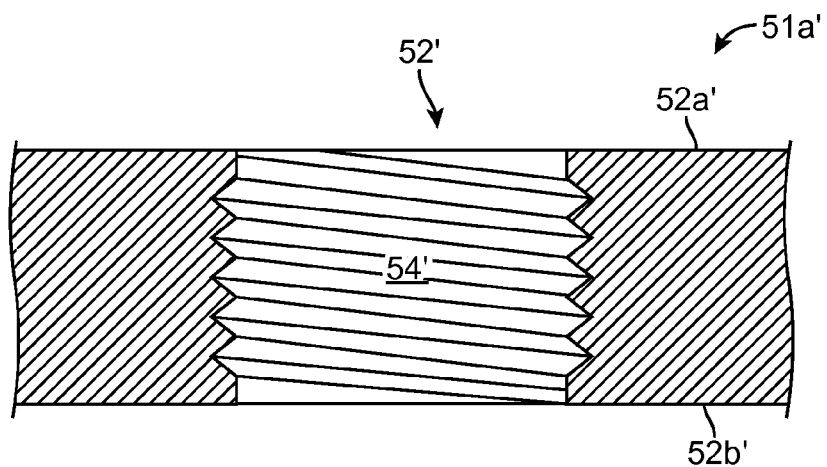
FIG. 6C is a side cross-sectional view of a link with marker hole having grooves according to another embodiment.

Grooves may be formed as spiral grooves as opposed to grooves that extend straight down (i.e., into the paper in FIGS. 6A-6B). Spiral grooves may be formed by a tapping tool such as a finely threaded drill bit or screw (about 1, 2, 3, 4, 5 or 4-10 threads per 100 microns). This structure is shown in FIG. 6C where a strut portion 51*a*' having an abluminal surface 52*a*' and hole 52' is tapped to produce one or more spiral grooves surface 54'. The hole 52' may have 2 to 10 threads per 100 microns, or a groove may have a pitch of about 10, 20, 30 or 50 microns.

Any combination of the Concept B and Concept C embodiments are contemplated. A hole may be polygonal such as rectangular, square or hexagonal with the grooves formed on walls. There may be 1, 2, 3, 4, 5-10, a plurality or grooves, grooves every 10, 20, 45, or 10-30 degrees about the perimeter of the hole. "Grooves" refers to either straight grooves (FIG. 6A-6B) or spiral grooves or threading (FIG. 6C). The grooves may be formed in a polygonal hole (e.g., square, rectangular, hexagonal) or elliptical hole (e.g., a circular hole).

D. Marker Having Concave Walls

Figures 8A, 8B:
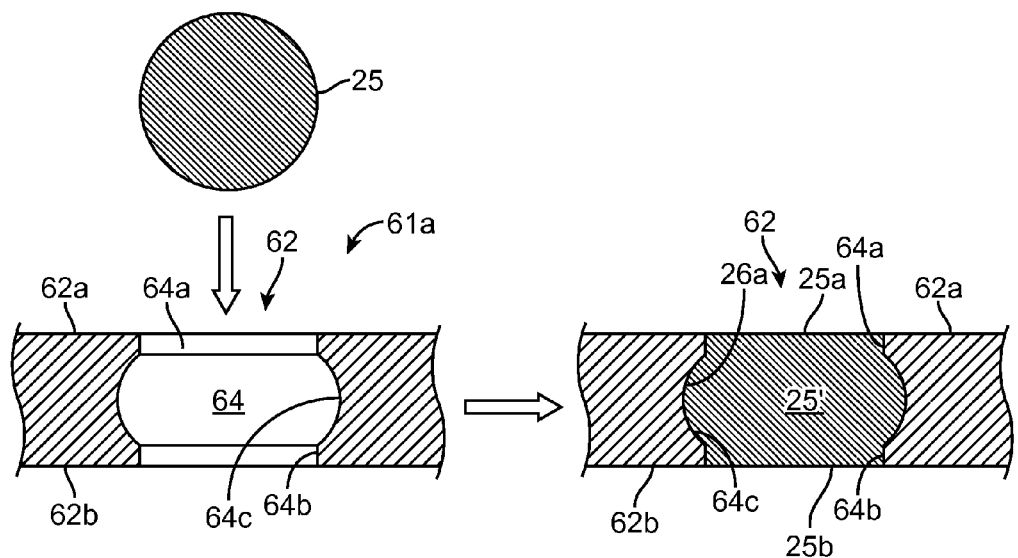
FIG. 8A is a partial side-cross sectional view of a link according to another embodiment. A spherical marker is being placed in a hole of the link.
FIG. 8B shows the link of FIG. 8A after the marker is placed in the hole.

According to Concept D, a marker hole has a concave surface between upper and lower rims to hold a marker in place. Referring to FIGS. 8A-8B, there is shown a strut portion 61*a* having an abluminal and luminal surface 62*a*, 62*b* respectively and a hole 62 to receive the marker 25, as shown. The wall 64 of the hole is cylindrical, like in the FIG. 2A embodiment, except that the wall 64 includes an annular and concave surface (or groove) formed about the perimeter. The (groove) surface 64*c* located between the upper and lower edges of the hole 62 is between an optional upper and lower rim 64*a*, 64*b* of the hole 62. The rims 64*a*, 64*b* help retain the marker 25 in the hole 62.

According to this embodiment a hole has a pseudomechanical interlock feature provided by the annular groove 64*c*. Referring to FIG. 8B the deformed marker 25' has a portion 26a generally taking the shape of the annular groove 64c having a concave shape, or displacing into the space defined by this part of the wall when the marker is forced into the hole. The rims 64a, 64b, and the convex shape of 25' nested into concave annular groove 64c, resist dislodgment of the marker 25' from the hole 62. As can be appreciated from FIG. 8B the marker 25' would have to deform before it dislodges from the hole 62. Because the marker 25' must deform to dislodge from the hole 62, the hole 62 having the annular groove 64c between upper and lower rims 64a, 64b provides a mechanical interlock. In contrast to other embodiments, the structure shown in FIG. 8B need not rely primarily or solely on friction and/or an adhesive/coating to secure the marker in place.

Figure 8C:
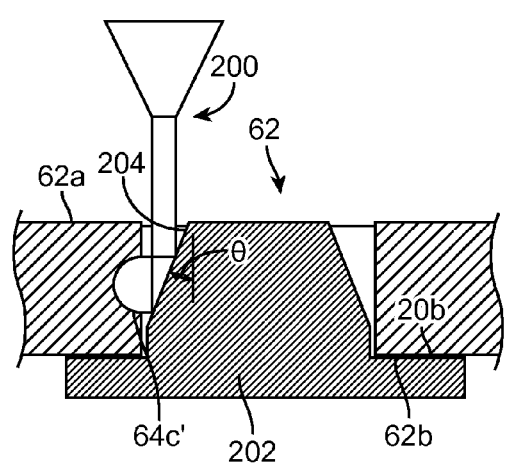
FIG. 8C shows a method for making the hole of FIG. 8A.

FIG. 8C illustrates a method for making the hole 62 according to Concept D using a laser 200 reflected off a reflective surface 204 of a reflector tool or reflector 202. The reflector 202 is frustoconical and is configured to extend up through the untapped hole 20. The reflector 202 is pressed and held against the luminal surface 62b to hold it in place. The reflective surface 204 is arranged at an angle of between 20 to 60 degrees with respect to the untapped wall of the hole 20. The surface 204 is arranged so that laser light impacts the wall 64c' at about a right angle as shown. The laser 200 is directed onto the surface 204, which reflects the light towards the wall and causes the laser energy to etch-out the groove. The laser is traced (or scanned) about the perimeter of the hole 20 to make the annular groove shown in FIG. 8A. The laser would trace a circle on the reflector 202, just inside the edges of the marker hole 20. The groove thickness (i.e., distance between the upper and lower rims 64a, 64b) can be up to about 60% to 80% and/or between about 20% to 50% of the strut thickness.

In the embodiments, the reflectors 202 having surface 204 can have a frustoconical part for each of the paired holes (FIG. 2), or instead have a set of hemispheres or cones for a set of marker holes An alternative laser reflector would be one which does not protrude into the marker bead hole but which presents a concave surface pressed up against the bottom of the hole with edges at surface 62b. A laser beam imping on this surface would be reflected against the opposite wall of hole 20. In another embodiment, the annular groove may instead be formed by a pin having an oblate spheroid shaped at its tip. The tip of the pin is forced into the hole 20 so that the tip sits within the hole. The hole is deformed to have an annular groove as shown in FIG. 8A. Then the marker 25 is pressed into the hole 62 to take a similar shape as in FIG. 8B.

E. Radiopaque Markers as Rivets

Figure 9A:
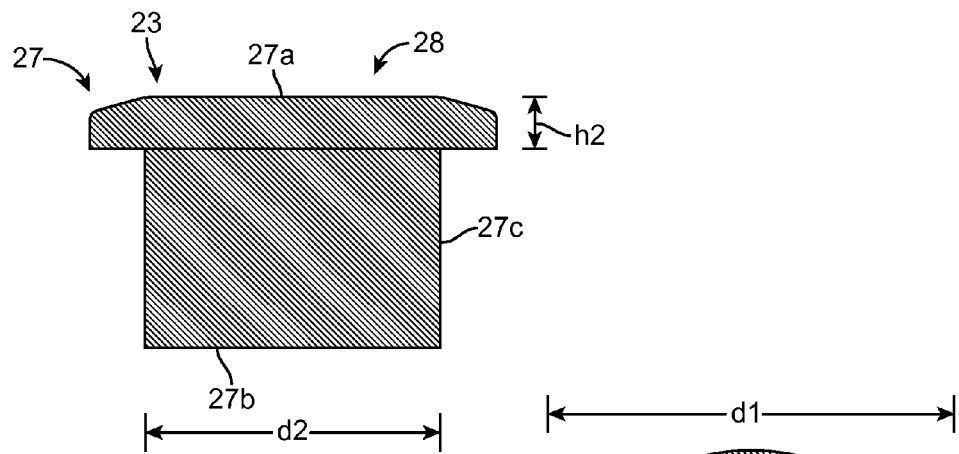
FIGS. 9A and 9B show a side and top view, respectively, of a marker according to another embodiment.
Figure 9B:
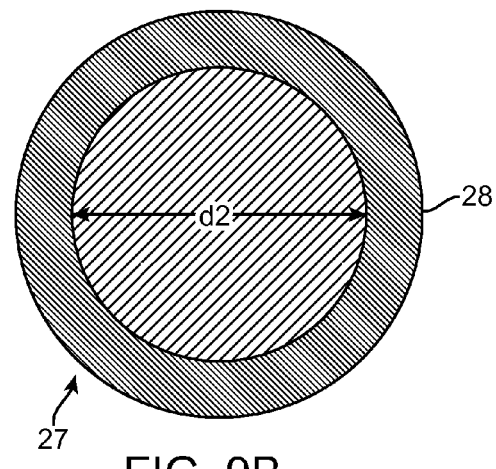

According to Concept E, a marker shaped as a rivet is used in place of the spherical marker 25. FIGS. 9A and 9B show respective side and top views of the marker 27 shaped as a rivet. The head 28 may include the abluminal surface 27a or luminal surface 27b of the rivet 27. In the drawings, the head 28 includes the abluminal surface 27a. It may be preferred to the have the head 28 be the luminal surface portion of the rivet 27 for assembly purposes, since then the scaffold may be placed over a mandrel and the tail portion of the rivet deformed by a tool (e.g., a pin) applied externally to the scaffold abluminal surface. The rivet 27 has a head diameter d1 and the shank 27c diameter d2 is about equal to the hole 22 diameter. The head 28 has a height of h2, which is about the amount the head 28 will extend beyond the abluminal surface 22a of the strut portion 21a. While not desirable, it may be an acceptable protrusion for a head 28 that does not extend more than about 25 microns, or from about 5 to 10 microns up to about 25 microns from the abluminal surface 22a, or a head that extends by an amount no more than about 25% of the strut thickness. The same extent of protrusion beyond the luminal surface 22b may be tolerated for the deformed tail of the rivet.

Figure 9C:
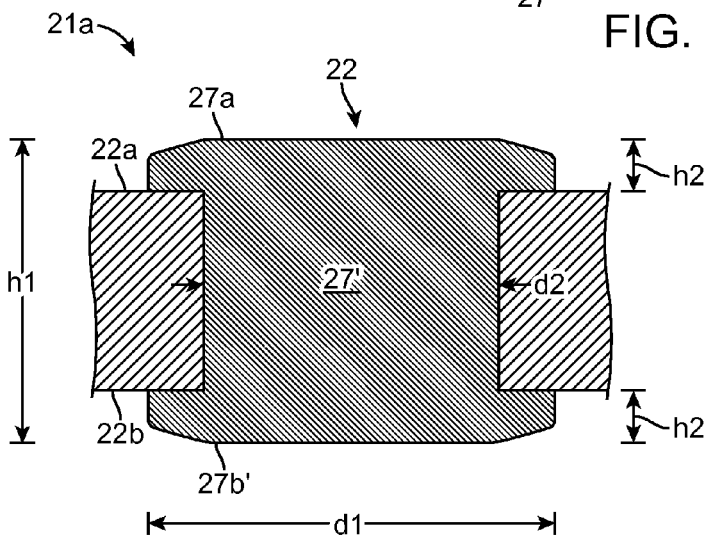
FIG. 9C is a cross-sectional view of a link having a hole and the marker of FIG. 9A embedded in the hole.

Referring to FIG. 9C there is shown the rivet in the hole 22. The deformed tail 27b' secures the rivet 27 in the hole 22. The overall height h1 is preferably not more than about 40% or about 10%-40% greater than the strut thickness (t) and the tail height is about the same as, or within 5 to 200 microns in dimension compared to the head height h2.

The rivet 27 may be attached to the hole 22 of the strut portion 21a by first inserting the rivet 27 into the hole 22 from the bore side of the scaffold so that the head 28 rests on the luminal surface 22b of the strut portion 21a. The scaffold is then slipped over a tight fitting mandrel. With the mandrel surface pressed against the head 28 a tool (e.g., a pin) is used to deform the tail 27b to produce the deformed tail 27b' in FIG. 9C. In some embodiments, the rivet 27 may be first inserted into the hole 22 from the abluminal side so that head 28 rests on the abluminal surface 22a of the strut portion 21a. With the head 28 held in place by a tool or flat surface applied against the abluminal surface, the tail 27b is deformed by a tool, pin, or mandrel which is inserted into the bore or threaded through the scaffold pattern from an adjacent position on the abluminal surface. In some embodiments the rivet 27 may be a solid body (FIG. 9A-9B) or a hollow body, e.g., the shank is a hollow tube and the opening extends through the head 28 of the rivet.

In some embodiments a rivet is a hollow or solid cylindrical tube and devoid of a pre-made head 28. In these embodiments the tube (solid or hollow) may be first fit within the hole then a pinch tool used to form the head and tail portions of the rivet.

Referring to FIGS. 10A-10B and 11A-11B there is shown embodiments for securing a marker using a starting cylindrical tube hollow (tube 65) or solid (tube 75), respectively.

Referring to FIGS. 10A-10B there is an attachment of a marker shaped as a hollow tube 65 placed into the strut portion 21a hole and deformed using a pinching tool 60. FIG. 10B shows the deformed marker 65'. The tube 65 has an inside cylindrical surface 67 and outer diameter that is about, or slightly greater than the hole 22 diameter. The tube has an undeformed length about equal to about 10%-40%, or 40%-80% greater than the strut thickness (t). The deformed tube/rivet has a deformed length (h2) of about 10-50% greater than the strut thickness and/or an undeformed length (h3) of about 15% to 70% greater than the strut thickness (t).

The pinching tool 60 includes an upper arm 60a and lower arm 60b. The deforming faces of the two arms 60a, 60b are the same. The face includes a deforming face 62a, 62b respectively shaped as an apex,point, hemisphere or convex surface, so that when pressed into the tube the end portions extending above the strut surface 22a, 22b respectively will be pushed outwardly, as shown in FIG. 10B. The arm's flattening surface 63a, 63b flattens the material against the strut surface. As can be appreciated from the drawings the deformed ends 65a', 65b' of the deformed tube 65' resemble the faces of the deforming faces 63a, 63b.

Referring to FIGS. 11A-11B there is an attachment of a marker shaped as a solid tube 75 placed into the strut portion 21a hole and deformed using a pinching tool 70. FIG. 11B shows the deformed marker 75'. The tube has an undeformed length about equal to about 10%-40%, or 40%-80% greater than the strut thickness (t). The deformed tube/rivet has a deformed length (h2) of about 10-50% greater than the strut thickness and/or an undeformed length (h3) of about 15% to 70% greater than the strut thickness (t).

The pinching tool 70 includes an upper arm 70a and lower arm 70b. The deforming faces of the two arms 70a, 70b are the same. The faces include a deforming face 72a for arm 70a and deforming face 72b for arm 70b, both of which may be shaped with an apex, point, hemisphere, or convex surface, so that when pressed into the tube the end portions extending above the strut surface 22a, 22b respectively will be pushed outwardly, as shown in FIG. 11B. The arm's flattening surface 73a, 73b flattens the material against the strut surface. As can be appreciated from the drawings the deformed ends 75a', 75b' of the deformed tube 75' resemble the faces of the deforming faces 73a, 72a, 73b, and 73a.

F. Use of a polygonal or irregular marker shape According to Concept F, an irregular-shaped marker having protruding edges is placed in a lased hole prior to a thermal process that shrinks the lased hole. Polymeric bioresorbable scaffolds may be laser cut from a tube. This thin wall, precision tubing can be fabricated by extrusion and expansion processes that include stretch blow molding. The tubing resulting from such processes is formed by deformation of the polymer, which can result in residual stresses remaining in the tube. Heating the tube above its glass transition temperature (Tg) releases these stresses and can be used advantageously to shrink features such as lased marker bead holes to increase securement of a previously placed radiopaque marker. In an alternative embodiment, the temperature of the scaffold is raised above the Tg of the tube material and the marker placed into the softer, heated polymer. This allows the polymer to become more compliant, or flow and thus allow a marker, particularly an irregularly shaped marker, to interact with the polymer surfaces to a greater degree, thereby raising the frictional forces and/or forming a mechanical fit, depending on the marker type used.

Figures 12A, 12B:
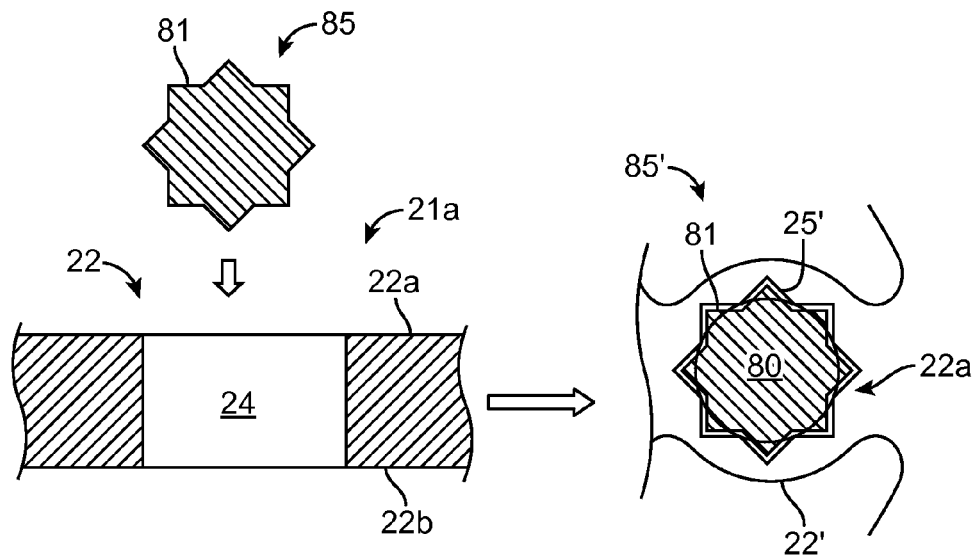
FIGS. 12A and 12B are cross-sectional views of a link and marker and method of attaching the marker to the link according to another embodiment.

Referring to FIGS. 12A and 12B there is shown an irregularly shaped marker 85 placed in the hole 22 of the strut portion 21a. The hole 22 may be at ambient temperature or at an elevated temperature (about 0-20 Degrees C. above the Tg of the strut material). Alternately, the hole 22 is heated above the Tg after the marker is inserted. The marker 85 has bumps, edges, corners or burrs 81 over its surface that when placed in the hole 22 deforms the hole, as illustrated in FIG. 12B. The engagement between the marker 85 and hole may form a mechanical interlock. For a marker with cylindrical symmetry, a degree of roughness can be defined as the maximum and minimum distances in terms of radius from the markers cylindrical axis (e.g., difference between inner and out diameter as a maximum degree of roughness, or % of inner or outer diameter). For the marker 85 this distance from max to min may be between 5 to 50% of the maximum marker diameter The marker may have a flower, star or polygonal shape to produce the same effect. When placed in the hole 22 the hole 22 deforms. The marker 85 may or may not deform, depending on the temperature of hole 22 and the hardness of the marker material.

G. Snap-in Marker

Figures 13A, 13B:
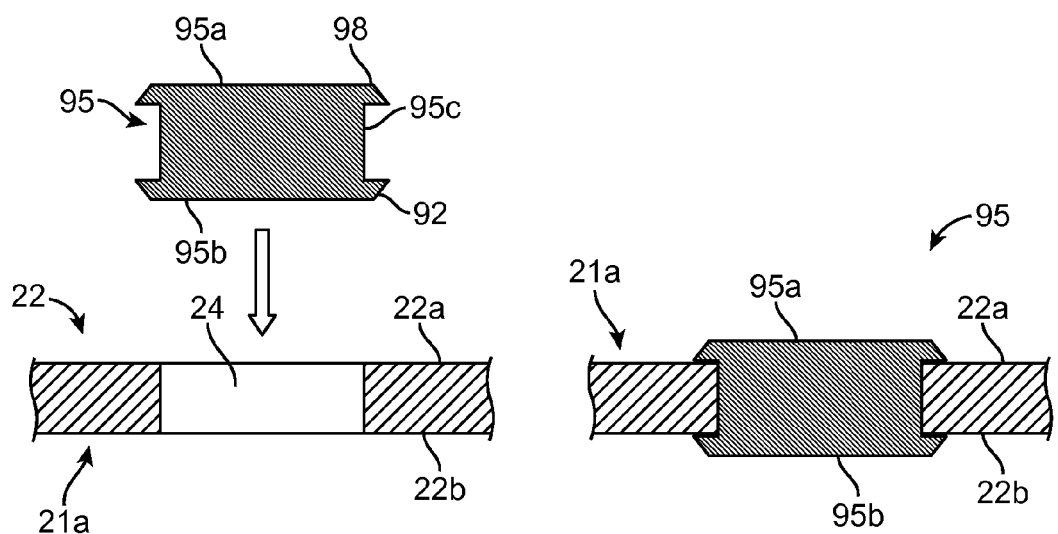
FIGS. 13A and 13B are cross-sectional views of a link and marker and method of attaching the marker to the link according to another embodiment.

According to Concept G, a snap-in marker is used. Referring to FIGS. 13A and 13B there is shown a marker 95 having a preformed head 98 and tail 92. The shank 95c of the marker has an extent about equal to that the hole 22, which in this case is a diameter. The length of the shank is about, slightly less, or slightly more than the strut thickness. In other embodiments the marker 95 may be rectangular, hexagonal or polygonal for fitting into the holes shown in FIG. 4A, 5A, 6A or 6C. The distance between abluminal surface 95a and luminal surface 95b in FIG. 13B satisfies inequality IE.2 or IE.4, defined below.

Platinum, and especially platinum/iridium alloys, are stronger than polymeric materials because they are metals. Many assembly and securement process use snap-fit parts where the tolerances and shapes are designed to hold parts together without fasteners. The main feature of the marker 95 is the head 98 and tail 92 having an enlarged diameter over the shank 95c part. There could be formed on portions 98 and 92 round ridges, or more wedge shaped features. When pressed in, the polymer will deform preferentially allowing the tail 92 or head 98 to pass through, or imbed within the hole to become partially or fully recessed within the hole 22. When the tail 92 or head 98 passes completely through hole 22, the polymer surface 22a or 22b will snap under marker feature 98 or 92, securing it and preventing movement in either direction.

With respect to any of Concepts A through G, the marker material may be platinum, platinum/iridium alloy, iridium, tantalum, palladium, tungsten, niobium, zirconium, or alloys thereof. The marker material may also be of biodegradable metals such as iron, zinc, magnesium, manganese or their alloys.

For some embodiments included under Concept A (e.g., the embodiments shown in FIGS. 3A-3C); some embodiments included under Concept E (e.g., the embodiments shown in FIGS. 9A-9C, 10A-10B and 11A-11B); and some embodiments included under Concept G (e.g., the embodiments shown in FIGS. 13A-13B) the following inequalities IE.1-IE.4 apply:

$$t \times (1.2) \leq L \leq t \times (1.8) \text{ or } 1.2 \leq (L/t) \leq 1.8 \qquad \text{IE.1}$$

$$t \times (1.1) \leq L' \leq t \times (1.5) \text{ or } 1.1 \leq (L'/t) \leq 1.5 \qquad \text{IE.2}$$

$$t \times (1.0) \leq L \leq t \times (1.8) \text{ or } 1.0 \leq (L/t) \leq 1.8 \qquad \text{IE.3}$$

$$t \times (1.0) \leq L' t \times (1.5) \text{ or } 1.0 \leq (L'/t) \leq 1.5 \qquad \text{IE.4}$$

Where:
  t is the average strut, bar arm or link thickness, or wall thickness of the tube from which the scaffold was made. The thickness t may vary between about 80 to 150 microns, 80 to 120 microns, 80 to 110 microns, 80 to 100 microns, or the thickness may be about 100 microns, or the thickness may be up to 130 or 140 microns;
  L is an undeformed length of the marker (Concept E); and
  L' is a deformed length of the marker (measured from the abluminal surface portion to the luminal surface portion for Concept E), length of the marker (Concept G), or distance between abluminal and luminal surfaces of a coating and/or polymer fill (Concept A).

Exemplary values for t are about 80 microns to 120 microns, or about 100 microns and L' or L being between about 100 microns and 150 microns.

The relations IE.1, IE.2, IE.3 and IE.4 reflect a need to maintain a low profile for struts exposed in the bloodstream, while ensuring the marker will be securely held in the strut. The concern addressed here is the degree thrombogenicity of the scaffold, which can be influenced by a strut thickness overall and/or protrusion from a strut surface. Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. Some of these factors are interrelated. The effect of strut thickness on acute thrombogenicity has been documented and studied both in vivo and in silico.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method for making a medical device, the method comprising:
providing a scaffold comprising a first polymer, the scaffold including a strut having a hole formed in the strut, wherein the hole has a hole volume and a hole opening located on a first side of the strut; and
attaching a marker to the scaffold, the marker comprising a radiopaque material and having a first end, a second end, and a medial portion between the first end and the second end, wherein the marker has a volume less than the hole volume, the attaching comprising the steps of:
press-fitting the marker into the hole, whereupon the medial portion engages the hole, the first end faces the hole opening, and the entire first end is recessed from the hole opening, thereby producing a space between the first end and the hole opening, and
filling at least a portion of the space with a second polymer,
thereby making the medical device.

2. The method of claim 1, wherein the second polymer is in a molten state or the second polymer is dissolved in a solvent when filling the at least the portion of the space with the second polymer.

3. The method of claim 2, wherein the at least a portion of the space is filled with a drug-polymer coating comprising the second polymer.

4. The method of claim 1, wherein the scaffold comprises a plurality of struts, the method further comprising the step of coating the plurality of struts with a third polymer after the filling step.

5. The method of claim 4, wherein the coating is a drug-polymer coating comprising the third polymer.

6. The method of claim 4, wherein a thickness TC measured from an abluminal surface to a luminal surface of the third polymer coating adjacent the marker is related to a distance L' measured from an abluminal surface to a luminal surface of the third polymer coating at the marker as $1.1 \leq L'/TC \leq 1.5$.

7. The method of claim 4, wherein the first polymer comprises poly(L-lactide), the scaffold has a wall thickness between 80 and 120 microns, and a distance L' measured from an abluminal surface to a luminal surface of the third polymer coating at the marker is between 100 microns and 150 microns.

8. The method of claim 1, wherein a bump comprising the second polymer covers the hole opening after the filling step.

9. The method of claim 8, wherein a wall thickness TS of a strut portion adjacent the marker is related to a distance L' measured from an abluminal surface to a luminal surface at the marker as $1.1 \leq L'/TS \leq 1.5$, where L' includes a distance of the bump that extends beyond the hole opening and TS.

10. The method of claim 1, wherein the strut has a first side and a second side and the hole has a first hole opening and a second hole opening located, respectively, on the first side and the second side, and the second end of the marker faces the second hole opening and the first end of the marker faces the first hole opening, and
wherein the filling step further includes depositing the second polymer in the second hole opening.

11. The method of claim 10, wherein the entire second end of the marker is recessed from the second hole opening, and the filling step further includes filling at least a portion of a space between the second end and the second hole opening.

12. The method of claim 1, wherein the marker is comprised of platinum, platinum/iridium alloy, iridium, tantalum, palladium, tungsten, niobium, zirconium, iron, zinc, magnesium, manganese, or alloys thereof.

13. The method of claim 1, wherein the hole is polygonal-shaped or has a roughened wall, and wherein at least one gap is present between the medial portion of the marker and the hole such that the filling step deposits the second polymer in the at least one gap.

* * * * *